United States Patent
Belldegrun et al.

(10) Patent No.: US 8,778,608 B2
(45) Date of Patent: Jul. 15, 2014

(54) CA9 GENE SINGLE NUCLEOTIDE POLYMORPHISMS PREDICT PROGNOSIS AND TREATMENT RESPONSE OF METASTATIC RENAL CELL CARCINOMA

(75) Inventors: Arie S. Belldegrun, Los Angeles, CA (US); Allan J. Pantuck, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 116 days.

(21) Appl. No.: 13/122,553

(22) PCT Filed: Oct. 8, 2009

(86) PCT No.: PCT/US2009/060064
§ 371 (c)(1), (2), (4) Date: Jun. 21, 2011

(87) PCT Pub. No.: WO2010/042765
PCT Pub. Date: Apr. 15, 2010

(65) Prior Publication Data
US 2011/0262391 A1 Oct. 27, 2011

Related U.S. Application Data

(60) Provisional application No. 61/103,895, filed on Oct. 8, 2008.

(51) Int. Cl.
*C12Q 1/68* (2006.01)
*C07H 21/02* (2006.01)
*C07H 21/04* (2006.01)

(52) U.S. Cl.
USPC ......... 435/6.11; 435/6.1; 435/6.14; 435/6.18; 536/23.2; 536/23.5; 536/24.31

(58) Field of Classification Search
None
See application file for complete search history.

(56) References Cited

FOREIGN PATENT DOCUMENTS

WO    WO 03/089659 A1    10/2003

OTHER PUBLICATIONS

Jacobs et al. The Christie National Aspiring Oncologist Conference. 2011, Oral Presentation 10, available via url: < manchester-oncology.org/file/MOS_Conference_2011.pdf.*
Hirschhorn et al. Genetics in Medicine. 2002. 4(2): 45-61.*
Hattersley et al. The Lancet. 2005. 366: 1315-1323.*
Lucentini et al. The Scientist (2004) vol. 18, p. 20.*
International Search Report and Written Opinion mailed Aug. 3, 2010 for International Application No. PCT/US2009/060064.
Anonymous: Reference SNP (refSNP) Cluster Report: rs12553173—(May 26, 2006) XP002568005 Retrieved from the Internet: URL:http://www.ncbi.nlm.nih.gov/SNP/snp_ref.cgi?rs=12553173>.
Anonymous: Single Nucleotide Polymorphism ss19787733—(Feb. 20, 2004) XP002568006 Retrieved from the Internet: URL:http://www.ncbi.nlm.nih.gov/SNP/snp_ss.cgi?subsnp_id=19787733>.
Anonymous Single Nucleotide Polymorphism ss52070605—(Mar. 29, 2006) XP002568007 Retrieved from the Internet: URL:http://www.ncbi.nlm.nih.gov/SNP/snp_ss.cgi?subsnp_id=52070605.
Atkins, Michael et al., "Carbonic Anhydrase IX Expression Predicts Outcome of Interleukin 2 Therapy for Renal Cancer," *Clin Cancer Res* (May 15, 2005) 11(10):3714-3721.
Li, Guorong et al., "CA9 gene expression in conventional renal cell carcinoma: a potential marker for prediction of early metastasis after nephrectomy," *Clin Exp Metastasis* (Mar. 28, 2007) 24:149-155.
Murakami, Y. et al., "M/CA9 gene expression as a potential biomarker in renal cell carcinoma," *BJU International* (Jan. 1, 1999) 83:743-747.
Ito, Noriyuki et al., "STAT3 Polymorphism Predicts Interferon-Alfa Response in Patients with Metastatic Renal Cell Carcinoma," *Journal of Clinical Oncology* (Jul. 1, 2007) 25(19):2785-2791.
De Martino, Michela et al., "CA9 Gene: Single Nucleotide Polymorphism Predicts Metastatic Renal Cell Carcinoma Prognosis," *Journal of Urology* (Aug. 1, 2009) 182(2):728-734.
Gardener, T. A. et al., "Prognostic Implications of Polymorphisms and Interleukin-2 Therapy for Renal Cell Carcinoma," *Journal of Urology* (Aug. 1, 2009) 182(2): 425-426.
De Martino, M. et al., "706 CA9 Gene Single Nucleotide Polymorphisms Predict Prognosis and Treatment Response of Metastic Reneal Cell Carcinoma," *European Urology Supplements* (Mar. 1, 2009) 8(4):297.
Petard, Jean-Jacques et al., "Recent Developments in Research on Kidney Cancer: Highlights from Urological and Oncological Congresses in 2007," *European Urology Supplements* (Feb. 19, 2008) 7(6)494-507.

* cited by examiner

*Primary Examiner* — Carla Myers
(74) *Attorney, Agent, or Firm* — Kilpatrick Townsend & Stockton LLP

(57) ABSTRACT

Methods and compositions for providing a prognosis or diagnosis for a human patient having renal cell cancer are provided. The method relates to the discovery of SNPs which are associated with a favorable prognosis and response to therapy in RCC.

7 Claims, 7 Drawing Sheets

Electropherograms showing wild type, heterozygous and homozygous sequences of the detected CA9 SNPs

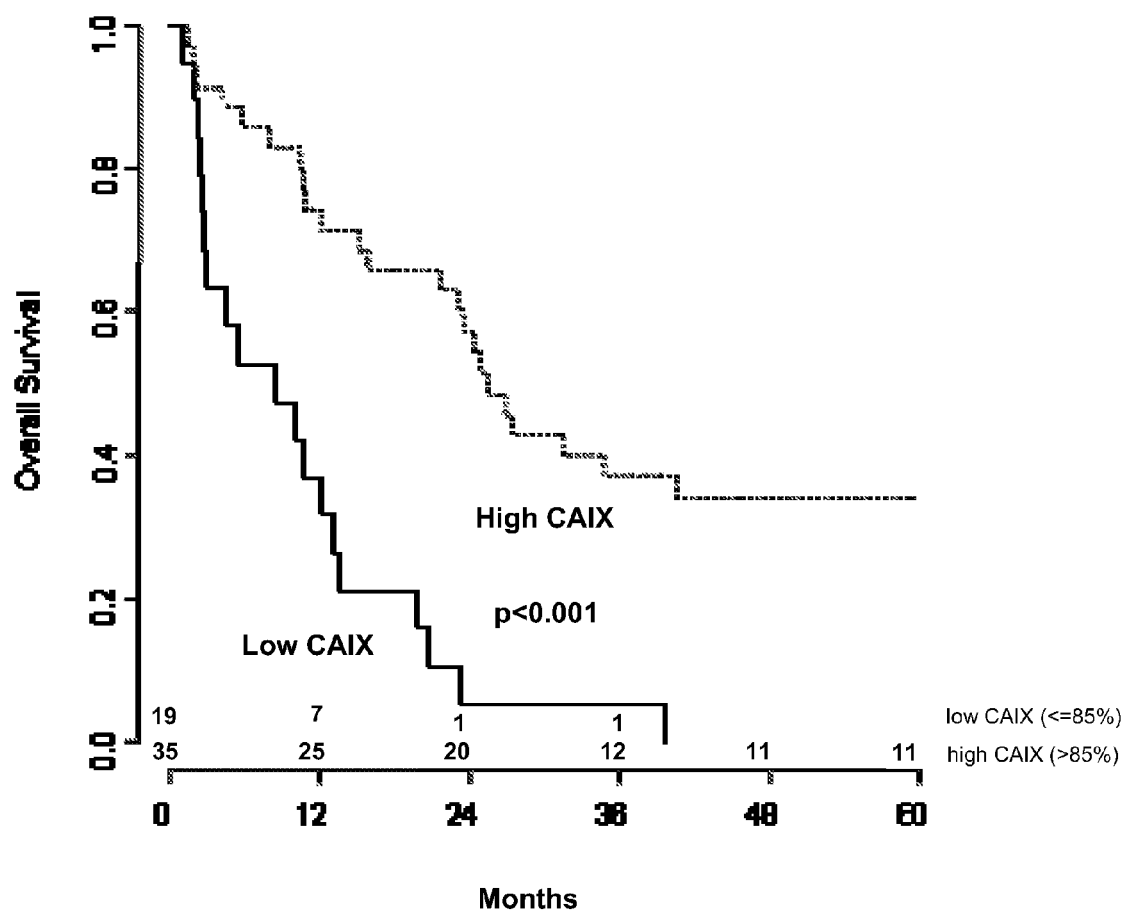

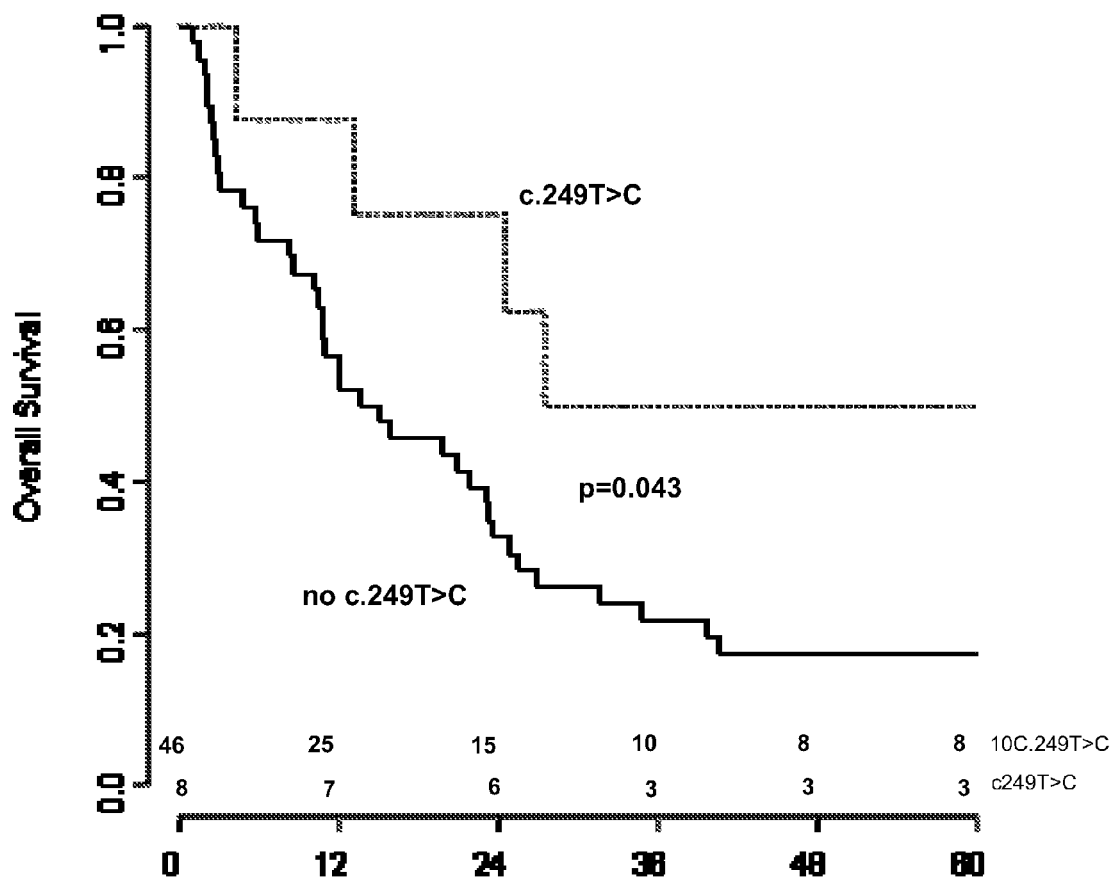

Figure 4

CAIX Protein Sequence (SEQ ID NO:1) NP_001207

MAPLCPSPWLPLLIPAPAPGLTVQLLLSLLLLVPVHPQRLPRMQEDSPLGGGSSGEDDPLGEEDLPSEEDSPREE
DPPGEEDLPGEEDLPGEEDLPEVKPKSEEEGSLKLEDLPTVEAPGDPQEPQNNAHRDKEGDDQSHWRYGGDPPWP
RVSPACAGRFQSPVDIRPQLAAFCPALRPLELLGFQLPPLPELRLRNNGHSVQLTLPPGLEMALGPGREYRALQL
HLHWGAAGRPGSEHTVEGHRFPAEIHVVHLSTAFARVDEALGRPGGLAVLAAFLEEGPEENSAYEQLLSRLEEIA
EEGSETQVPGLDISALLPSDFSRYFQYEGSLTTPPCAQGVIWTVFNQTVMLSAKQLHTLSDTLWGPGDSRLQLNF
RATQPLNGRVIEASFPAGVDSSPRAAEPVQLNSCLAAGDILALVFGLLFAVTSVAFLVQMRRQHRRGTKGGVSYR
PAEVAETGA

Figure 5

CAIX Nucleic Acid cDNA Sequence (SEQ ID NO:2) NM_001216.2

```
   1 gcccgtacac accgtgtgct gggacacccc acagtcagcc gcatggctcc cctgtgcccc
  61 agccctggc tccctctgtt gatcccggcc cctgctccag gcctcactgt gcaactgctg
 121 ctgtcactgc tgcttctggt gcctgtccat ccccagaggt tgccccggat gcaggaggat
 181 tccccttgg gaggaggctc ttctggggaa gatgacccac tgggcgagga ggatctgccc
 241 agtgaagagg attcacccag agaggaggat ccacccgag aggaggatct acctggagag
 301 gaggatctac ctggagagga ggatctacct gaagttaagc ctaaatcaga agaagagggc
 361 tccctgaagt tagaggatct acctactgtt gaggctcctg gagatcctca gaaccccag
 421 aataatgccc acagggacaa gaaggggat gaccagagtc attggcgcta tggaggcgac
 481 ccgcctggc cccgggtgtc cccagcctgc gcgggcgct tccagtcccc ggtggatatc
 541 cgccccagc tgccgccttt ctgccggcc ctgcgccccc tggaactcct gggcttccag
 601 ctcccgccgc tcccagaact gcgcctgcgc aacaatggcc acagtgtgca actgaccctg
 661 cctctgggc tagatggc tctggtccc gggcgggagt accgggctct gcagctgcat
 721 ctgcactggg gggctgcagg tcgtccgggc tggagcaca ctgtggaagg ccaccgtttc
 781 cctgccgaga tccacgtggt tcacctcag accgccttg ccagagttga cgaggccttg
 841 gggcgcccgg gaggcctggc cgtgttggcc gcctttctgg aggagggcc ggaagaaaac
 901 agtgcctatg agcagttgct gtctcgcttg gaagaaatcg ctgaggaagg ctcagagact
 961 caggtcccag gactggacat atctgcactc ctgccctctg acttcagccg ctacttccaa
1021 tatgagggt ctctgactac accgccctgt gcccaggtg tcatctggac tgtgtttaac
1081 cagacagtga tgctgagtgc taagcagctc cacaccctct ctgacaccct gtggggacct
1141 ggtgactctc ggctacagct gaacttccga gcgacgcagc ctttgaatgg gcgagtgatt
1201 gaggcctcct tccctgctgg agtggacagc agtcctcggg ctgctgagcc agtccagctg
1261 aattcctgcc tggctgctgg tgacatccta gccctggttt ttggcctcct ttttgctgtc
1321 accagcgtcg cgttccttgt gcagatgaga aggcagcaca aaggggaac caaaggggt
1381 gtgagctacc gcccagcaga ggtagccgag actggagcct agaggctgga tcttggagaa
1441 tgtgagaagc agccagagg catctgaggg ggagccggta actgtcctgt cctgctcatt
1501 atgccacttc cttttaactg ccaagaaatt ttttaaaata aatatttata ataaaaaaaa
1561 a
```

Figure 6A

NCBI Entrez Gene database: CA9 carbonic anhydrase IX [ Homo sapiens ] GeneID: 768 updated 06-Sep-2009; NCBI Reference Sequence: NC_000009.11. ACCESSION   NC_000009 REGION: 35673915..35681156 GPC_000000033

```
         CAIX Genomic Sequence (SEQ ID NO:3)
   1 gcccgtacac accgtgtgct gggacacccc acagtcagcc gcatggctcc cctgtgcccc
  61 agccctggc tccctctgtt gatcccggcc cctgctccag gcctcactgt gcaactgctg
 121 ctgtcactgc tgcttctggt gcctgtccat ccccagaggt tgccccggat gcaggaggat
 181 tccccttgg gaggaggctc ttctggggaa gatgacccac tgggcgagga ggatctgccc
 241 agtgaagagg attcacccag agaggaggat ccacccggag aggaggatct acctggagag
 301 gaggatctac ctggagagga ggatctacct gaagttaagc ctaaatcaga agaagagggc
 361 tccctgaagt tagaggatct acctactgtt gaggctcctg gagatcctca agaacccag
 421 aataatgccc acaggacaa agaaggtaag tggtcatcaa tctccaaatc caggttccag
 481 gaggttcatg actcccctcc catacccag cctaggctct gttcactcag ggaaggaggg
 541 gagactgtac tccccacaga agcccttcca gaggtcccat accaatatcc ccatcccac
 601 tctcggaggt agaaagggac agatgtggag agaaaataaa aagggtgcaa aaggagagag
 661 gtgagctgga tgagatggga gagaagggg aggctggaga agagaaaggg atgagaactg
 721 cagatgagag aaaaaatgtg cagacagagg aaaaaaatag gtggagaagg agagtcagag
 781 agtttgaggg gaagagaaaa ggaaagcttg ggaggtgaag tgggtaccag agacaagcaa
 841 gaagagctag tagaagtcat ctcatcttag gctacaatga ggaaattgag acctaggaag
 901 aagggacaca gcaggtagag aaacgtggct tcttgactcc caagccagga atttgggaa
 961 agggggttgga gaccatacaa ggcagaggga tgagtgggga gaagaaagaa gggagaaagg
1021 aaagatggtg tactcactca tttgggactc aggactgaag tgcccactca ctttttttttt
1081 tttttttttt gagacaaact ttcacttttg ttgcccaggc tggagtgcaa tggcgcgatc
1141 tcggctcact gcaacctcca cctcccgggt tcaagtgatt ctcctgcctc agcctctagc
1201 caagtagctg cgattacagg catgcgccac cacgccggc taatttttgt attttttagta
1261 gagacgggggt ttcgccatgt tggtcaggct ggtctcgaac tcctgatctc aggtgatcca
1321 accaccctgg cctcccaaag tgctgggatt ataggcgtga gccacagcgc ctggcctgaa
1381 gcagccactc acttttacag accctaagac aatgattgca agctggtagg attgctgttt
1441 ggcccaccca gctgcggtgt tgagtttggg tgcggtctcc tgtgctttgc acctgcccg
1501 cttaaggcat ttgttacccg taatgctcct gtaaggcatc tgcgtttgtg acatcgtttt
1561 ggtcgccagg aagggattgg ggctctaagc ttgagcggtt catccttttc atttatacag
1621 gggatgacca gagtcattgg cgctatggag gtgagacacc caccgctgc acagacccaa
1681 tctgggaacc cagctctgtg gatctcccct acagccgtcc ctgaacactg gtcccgggcg
1741 tcccacccgc cgcccaccgt cccacccct cacctttttc accgggttc cctaagttcc
1801 tgacctaggc gtcagacttc ctcactatac tctcccaccc caggcgaccc gccctggccc
1861 cgggtgtccc cagcctgcgc gggccgcttc cagtccccgg tggatatccg ccccagctc
1921 gccgccttct gcccggccct gcgccccctg gaactcctgg gcttccagct cccgccgctc
1981 ccagaactgc gcctgcgcaa caatggccac agtggtgagg gggtctcccc gccgagactt
2041 ggggatgggg cggggcgcag ggaagggaac cgtcgcggca gtgcctgccc ggggggttggg
2101 ctgccctac cgggcgggc cggctcactt gcctctccct acgcagtgca actgaccctg
2161 cctcctgggg tagagatggc tctgggtccc gggcgggagt accgggctct gcagctgcat
2221 ctgcactggg gggctgcagg tcgtccgggc tcggagcaca ctgtggaagg ccaccgtttc
2281 cctgccgagg tgagcgcgga gctgccgag aaggggcaaa ggagcggggc ggagcggggc
2341 cagagacgtg gccctctcct accctcgtgt ccttttcaga tccacgtggt tcacctcagc
2401 accgcctttg ccagagttga cgaggccttg gggcgcccgg gaggcctggc cgtgttggcc
2461 gcctttctgg aggtaccaga tcctggacac ccctactcc ccgctttccc atcccatgct
2521 cctcccggac tctatcgtgg agccagagac cccatcccag caagctcact caggccctg
2581 gctgacaaac tcattcacgc actgttttgtt catttaacac ccactgtgaa ccaggcacca
2641 gccccaaca aggattctga agctgtaggt ccttgcctct aaggagccca cagccagtgg
2701 gggaggctga catgcagac acataggaag gacatagtaa agatggtggt cacagaggag
2761 gtgacactta aagccttcac tggtagaaaa gaaaggagg tgttcattgc agaggaaaca
2821 gaatgtgcaa agactcagaa tatggcctat ttagggaatg gctacataca ccatgattag
2881 aggaggccag taaagggaag ggatggtgag atgcctgcta ggttcactca ctcacttta
```

Figure 6B

```
2941 tttatttatt tattttttg acagtctctc tgtcgcccag gctggagtgc agtggtgtga
3001 tcttgggtca ctgcaacttc cgcctcccgg gttcaaggga ttctcctgcc tcagcttcct
3061 gagtagctgg ggttacaggt gtgtgccacc atgcccagct aattttttt tgtattttta
3121 gtagacaggg tttcaccatg ttggtcaggc tggtctcaaa ctcctggcct caagtgatcc
3181 gcctgactca gcctaccaaa gtgctgatta caagtgtgag ccaccgtgcc cagccacact
3241 cactgattct taatgccag ccacacagca caaagttcag agaaatgcct ccatcatagc
3301 atgtcaatat gttcatactc ttaggttcat aatgttctta acattaggtt cataagcaaa
3361 ataagaaaaa agaataataa ataaagaag tggcatgtca ggacctcacc tgaaaagcca
3421 aacacagaat catgaaggtg aatgcagagg tgacaccaac acaaaggtgt atatatggtt
3481 tcctgtgggg agtatgtacg gaggcagcag tgagtgagac tgcaaacgtc agaagggcac
3541 gggtcactga gagcctagta tcctaagtaa agtgggctct ctcctctct ctccagcttg
3601 tcattgaaaa ccagtccacc aagcttgttg gttcgcacag caagagtaca tagagtttga
3661 aataatacat aggattttaa gagggagaca ctgtctctaa aaaaaaaaac aacagcaaca
3721 acaaaaagca acaaccatta caattttatg ttccctcagc attctcagag ctgaggaatg
3781 ggagaggtct atgggaaccc cccttcatgt tccggccttc agccatggcc ctggatacat
3841 gcactcatct gtcttacaat gtcatccccc aggagggccc ggaagaaaac agtgcctatg
3901 agcagttgct gtctcgcttg gaagaaatcg ctgaggaagg tcagtttgtt ggtctggcca
3961 ctaatctctg tggcctagtt cataaagaat caccctttgg agcttcaggt ctgaggctgg
4021 agatgggctc cctccagtgc aggagggatt gaagcatgag ccagcgctca tcttgataat
4081 aaccatgaag ctgacagaca cagttacccg caaacggctg cctacagatt gaaaaccaag
4141 caaaaaccgc cgggcacggt ggctcacgcc tgtaatccca gcactttggg aggccaaggc
4201 aggtggatca cgaggtcaag agatcaagac catcctggcc aacatggtga accccatct
4261 ctactaaaaa tacgaaaaaa tagccaggcg tggtggcggg tgcctgtaat cccagctact
4321 cgggaggctg aggcaggaga atggcatgaa cccgggaggc agaagttgca gtgagccgag
4381 atcgtgccac tgcactccag cctgggcaac agagcgagac tcttgtctca aaaaaaaaaa
4441 aaaaaagaa aaccaagcaa aaccaaaat gagacaaaaa aaacaagacc aaaaatggt
4501 gtttggaatt gtcaaggtca agtctggaga gctaaacttt tctgagaac tgtttatctt
4561 taataagcat caaatatttt aactttgtaa atacttttgt tggaaatcgt tctcttctta
4621 gtcactcttg ggtcattta aatctcactt actctactag accttttagg tttctgctag
4681 actaggtaga actctgcctt tgcatttctt gtgtctgttt tgtatagtta tcaatattca
4741 tatttattta caagttattc agatcatttt ttcttttctt ttcttttttt ttttttttac
4801 atctttagta gagacagggt ttcaccatat tggccaggct gctctcaaac tcctgacctt
4861 gtgatccacc agcctcggcc tcccaaagtg ctgggattca ttttttcttt ttaatttgct
4921 ctgggcttaa acttgtggcc cagcacttta tgatggtaca cagagttaag agtgtagact
4981 cagacggtct ttcttctttc cttctcttcc ttcctccctt ccctcccacc ttcccttctc
5041 tccttccttt ctttcttcct ctcttgcttc ctcaggcctc ttccagttgc tccaaagccc
5101 tgtacttttt tttgagttac gtcttatggg aagggcctgc acttagcgaa gaagtggtct
5161 cagagttgag ttaccttggc ttctgggagg tgaaactgta tccctatacc ctgaagcttt
5221 aaggggtgc aatgtagatg agacccaac atagatcctc ttcacaggct cagagactca
5281 ggtcccagga ctggacatat ctgcactcct gccctctgac ttcagccgct acttccaata
5341 tgagggtct ctgactacac cgccctgtgc caggtgtc atctggactg tgtttaacca
5401 gacagtgatg ctgagtgcta agcaggtggg cctggggtgt gtgtggcac agtgggtgcg
5461 ggggaaagag gatgtaagat gagatgagaa acaggagaag aaagaaatca aggctgggct
5521 ctgtggctta cgcctataat cccaccacgt tgggaggctg aggtgggaga atggtttgag
5581 cccaggagtt caagacaagg cggggcaaca tagtgtgacc ccatctctac caaaaaaacc
5641 ccaacaaaac caaaatagc cgggcatggt ggtatgcgcc tagtcccagc tactcaagga
5701 ggctgaggtg ggaagatcgc ttgattccag gagtttgaga ctgcagtgag ctatgatccc
5761 accactgcct accatcttta ggatacattt atttatttat aaaagaaatc aagaggctgg
5821 atggggaata caggagctgg agggtggagc cctgaggtgc tggttgtgag ctggcctggg
5881 acccttgttt cctgtcatgc catgaaccca cccacactgt ccactgacct ccctagctcc
5941 acacctctc tgacacctg tggggacctg gtgactctcg gctacagctg aacttccgag
6001 cgacgcagcc tttgaatggg cgagtgattg aggcctcctt ccctgctgga gtggacagca
6061 gtcctcgggc tgctgagcca ggtacagctt tgtctggttt cccccagcc agtagtccct
6121 tatcctccca tgtgtgtgcc agtgtctgtc attggtggtc acagcccgcc tctcacatct
6181 ccttttctc tccagtccag ctgaattcct gctggctgc tggtgagtct gcccctcctc
6241 ttggtcctga tgccaggaga ctcctcagca ccattcagcc ccagggctgc tcaggaccgc
```

Figure 6C

```
6301 ctctgctccc tctccttttc tgcagaacag accccaaccc caatattaga gaggcagatc
6361 atggtgggga ttcccccatt gtccccagag gctaattgat tagaatgaag cttgagaaat
6421 ctcccagcat ccctctcgca aaacaatccc ccccttttt ttaaagatag ggtctcactc
6481 tgttgcccag gctggggtgt tgtggcacga tcatagctca ctgcagcctc gaactcctag
6541 gctcaggcaa tcctttcacc ttagcttctc aaagcactgg gactgtaggc atgagccact
6601 gtgcctggcc ccaaacggcc cttttacttg gcttttagga agcaaaaacg gtgcttatct
6661 taccccttct cgtgtatcca ccctcatccc ttggctggcc tcttctggag actgaggcac
6721 taggggctgc ctgagaactc ggggcagggg tggtggagtg cactgaggca ggtgttgagg
6781 aactctgcag accctcttc cttcccaaag cagccctctc tgctctccat cgcaggtgac
6841 atcctagccc tggttttgg cctccttttt gctgtcacca gcgtcgcgtt ccttgtgcag
6901 atgagaaggc agcacaggta ttacactgac cctttcttca ggcacaagct tcccccaccc
6961 ttgtggagtc acttcatgca aagcgcatgc aaatgagctg ctcctgggcc agttttctga
7021 ttagccttc ctgttgtgta cacacagaag gggaaccaaa gggggtgtga gctaccgccc
7081 agcagaggta gccgagactg gagcctagag gctggatctt ggagaatgtg agaagccagc
7141 cagaggcatc tgaggggag ccggtaactg tcctgtcctg ctcattatgc cacttcctt
7201 taactgccaa gaaattttt aaaataaata tttataataa aa
```

CA9 GENE SINGLE NUCLEOTIDE POLYMORPHISMS PREDICT PROGNOSIS AND TREATMENT RESPONSE OF METASTATIC RENAL CELL CARCINOMA

CROSS-REFERENCES TO RELATED APPLICATIONS

This application claims the benefit of U.S. Provisional Patent Application No. 61/103,895 filed Oct. 8, 2008, the disclosure of which is hereby incorporated herein by reference in its entirety for all purposes.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable

FIELD OF THE INVENTION

The present invention relates to single base polymorphisms in the CAIX gene and their use in the prognosis, diagnosis and therapy for metastatic renal cell carcinoma (MRCC).

BACKGROUND OF THE INVENTION

Every year, over 12,000 Americans succumb to metastatic renal cell carcinoma (MRCC) [1]. The prognosis of this disease is poor and the median survival time is only 1-2 years [2]. Chemotherapy is ineffective [3] with the notable exception of rare tumors with sarcomatoid features [4]. Until recently, cytokine-based immunotherapy was the only effective therapeutic approach, however, response rates were low and the treatment was accompanied by substantial side effects. Identification of reliable predictors of response and survival are necessary to choose patients who most likely benefit from these drugs. This question is now even more pertinent since the approval of sorafenib, sunitinib and temsirolimus has expanded the therapeutic options available to MRCC patients. Currently clinical and laboratory information may distinguish different groups [5], but molecular information such as protein [6, 7] or genetic data [8, 9] may further improve pre-therapeutic risk assessment.

A Single Nucleotide Polymorphism (SNP) is a variation in the DNA sequence, which occurs when a nucleotide (A, T, C or G) is changed in at least 1% of a certain population. When a SNP falls in a coding sequence, it may determine a change of an amino acid in the related protein sequence. Such a SNP is called non-synonymous. In accordance with the degeneracy rules of the genetic code, a SNP could also generate the same amino acid, which is than called a synonymous SNP. Of note, several studies have indicated that a SNP in a non-coding region of a gene may also impact biological processes.

SNPs in the human genome contribute to wide variations in how individuals respond to medications, either by changing the pharmacokinetics of drugs or by altering the cellular response to therapeutic agents [10]. Several studies have assessed the importance of these SNPs in predicting prognosis and response to therapies and drugs. For example, SNPs have been associated with prognosis of breast cancer, lymphoid neoplasms, and nasopharyngeal carcinoma [1]-[17]. In RCC, Ito et al. [8] found that a SNP in the Signal Transducer and Activator 3 gene (STAT3) is associated with a greater likelihood of response to interferon-alpha.

The carbonic anhydrase 9 gene (CA9) is located on chromosome 9p12-13, which represents a chromosomal area linked to prognosis in RCC [18-20]. CA9 comprises 11 exons and encodes for the 459 amino acid protein CAIX. CAIX is a membrane associated protein and catalyzes the reversible reaction $H_2O+CO_2 \leftrightarrow H^+ + HCO_3^-$, which is crucial to a wide variety of processes including pH regulation. CAIX is not expressed in the majority of benign organs and tissues, but abundantly expressed as a direct consequence of hypoxia in numerous cancers [21]. Studies demonstrate that high CAIX expression in clear cell RCC is associated with better prognosis and a greater likelihood of response to IL-2 based immunotherapy [22, 23]. Taken together, CA9 is located in a prognostically relevant chromosomal area and is encoding for one of the most significant protein markers in metastatic RCC. In contrast to CAIX protein, however, no efforts have been made to date to study the CA9 gene in metastatic RCC. Here, we test the hypotheses that SNPs and mutations of the CA9 gene are associated with CAIX expression, response to immunotherapy and survival in metastatic rCC.

At present, there are several FDA-approved drugs available for the treatment of MRCC, namely IL-2, sunitinib, sorafenib, and temsirolimus [39-41]. Pre-therapeutic prognostic assessment is required to select patients most likely to benefit from certain agents. However, only a few reliable predictors of response and survival are currently available. Motzer et al. [5] utilized clinical (performance status, time from diagnosis to start of therapy) and laboratory data (lactate dehydrogenase, hemoglobin, and corrected calcium levels) to predict survival of patients treated with interferon-alpha. Zisman et al. [42] stratified patients with MRCC into three prognostic groups based on stage, performance status and Fuhrman grade. Protein expression in the tumor and genetic information may further assist in prognostic assessment. Kim et al. [6] assessed 8 molecular markers in MRCC and found that CAIX, PTEN, p53, and vimentin expression significantly enhanced the predictive accuracy of a clinical prognostic model. Ito et al. [8] analyzed a cohort of 75 Japanese MRCC patients treated with interferon-alpha. They found that rs4796743, which is located in the non-coding 5'-flanking region of STAT3 gene, is associated with a 2.7 fold greater likelihood of response to interferon-alpha.

A leading treatment for MRCC is immunotherapy with IL-2. This treatment is associated with severe toxicities. Accordingly, there is a need to identify patients for whom IL-2 would be of sufficient benefit to warrant the health risks. This invention provides for this need by providing a means for identifying such patients.

BRIEF SUMMARY OF THE INVENTION

The present invention relates to Applicant's discovery that CA9 SNPs are frequently found in patients with MRCC. The C allele variant rs12553173 in particular is associated with improved overall survival and a greater likelihood of response to IL-2. The Applicants have further found that CA9 rs12553173 and CAIX expression levels are both independent prognostic factors of overall survival and complementary in predicting prognosis of MRCC.

Accordingly, in a first aspect the invention concerns a method of providing a prognosis for MRCC in which the presence of the C allele variant rs12553173 is associated with a substantially improved likelihood of survival and response to IL-2 therapy as compared to those MRCC patients lacking the variant. In one preferred embodiment of the above, the polymorphic site is the synonymous SNP rs12553173 (c.249T>C) (corresponding to conversion of a T to a C at position 187 of SEQ ID NOS:2 and 3) (SNP1).

In this aspect, the invention provides methods for providing a prognosis for renal cell cancer (RCC) or MRCC for a human patient in need thereof, the method comprising the steps:

a) identifying the nucleotide(s) present at one or more polymorphic sites in the CA9 nucleic acid from the patient; and b) providing the prognosis, wherein the prognosis is according to the nucleic acid identified at the polymorphic site.

In a another embodiment, the invention provides methods for providing a prognosis for renal cell cancer (RCC) or MRCC for a patient in need thereof, the method comprising the steps:

a) obtaining sample of CA9 nucleic acid from the patient;

b) identifying the nucleotide(s) present at one or more polymorphic sites in the CA9 nucleic acid; and c) providing the prognosis, wherein the prognosis is according to the nucleic acid identified at the polymorphic site.

In other embodiments of this aspect, the CA9 nucleic acid is genomic DNA or cDNA or mRNA. In a particularly preferred embodiment, the polymorphic site corresponds to SNP1 and the identification of the presence of a C residue at the SNP position indicates that the patient is a good candidate for, or likely to respond to, immunotherapy (e.g., therapy with IL-2). The prognosis may be provided to the patient and/or used to guide therapy. In another particularly preferred embodiment, the polymorphic site corresponds to SNP1 and the identification of the presence of a C residue at the SNP1 position indicates that the patient has better odds of overall survival.

In yet another embodiment, the invention provides a method of treating a patient having RCC or MRCC, the method comprising:

a) identifying the nucleotide(s) present at one or more polymorphic sites in CA9 nucleic acid obtained from the patient; and b) treating the patient, or selecting the patient for treatment, with immunotherapy according to the identification of the nucleotide(s) at the polymorphic site. In a preferred embodiment, polymorphic site is SNP1 and the identification of a C residue at the SNP1 position in the CA9 nucleic acid leads the patient to be treated, or selected for treatment, with immunotherapy (e.g., IL-2). In preferred embodiments, the CA9 nucleic acid is genomic DNA or cDNA or mRNA.

In an other embodiment, the invention provides a method of treating a patient having RCC or MRCC, the method comprising:

a) obtaining a sample of CA9 nucleic acid from the patient;

b) identifying the nucleotide(s) present at one or more polymorphic sites in the CA9 nucleic acid; and c) wherein the patient is treated, or selected for treatment, for immunotherapy according to the identification of the nucleotide(s) at the polymorphic site. In a preferred embodiment, polymorphic site is SNP1 and the identification of a C residue at the SNP1 position in the CA9 nucleic acid leads the patient to be treated, or selected for treatment, with immunotherapy (e.g., IL-2). In preferred embodiments, the CA9 nucleic acid is genomic DNA or cDNA or mRNA.

Further embodiments of the above, the level of expression of CA9 nucleic acid or protein is also determined for a cancer tissue sample. The expression can be determined by measuring tissue levels of the protein or the nucleic acid in the tissue.

The present invention also relates to allelic variants of CA9 and provides allele-specific nucleic acid primers and probes suitable for detecting these allelic variants for applications such as molecular diagnosis, prediction of an individual's MRCC susceptibility and appropriate therapy, personalized medicine, and/or the genetic analysis of the CA9 gene in a population.

In a this aspect, the invention provides oligonucleotides from 10 to 40 nucleotides in length each of which is identical in sequence to a corresponding sequence of CA9 which is at most 500, 400, 300, 200 or 100 nucleotides from a polymorphic site. Pairs of the nucleotides are useful in amplifying a CA9 nucleic acid comprising the polymorphic site, for example, in a polymerase chain reaction (PCR) or in a reverse-transcriptase (RT)-PCR reaction. In particular, the present invention provides an isolated nucleic acid comprising a sequence identical to that of variant CA9 gene which can be used use in identifying the nucleotides present a the polymorphic sites. In one embodiment of the above, the polymorphic site is the synonymous SNP rs12553173 (c.249T>C) (corresponding to conversion of a T to a C at position 187 of SEQ ID NOS:2 and 3) (SNP1).

The invention further provides diagnostic kits comprising one or more allele-specific oligonucleotide for SNP1, and also may include one or more primers for use in amplifying a nucleic acid having a SNP site according to the invention (e.g., SNP1).

In any of the above aspects, a preferred SNP is SNP1.

BRIEF DESCRIPTION OF THE DRAWINGS

FIG. 2. Overall survival according to CAIX expression. The numbers of patients at risk are indicated.

FIG. 3. Overall survival according to CA9 SNP rs12553173 (c.249T>C). The numbers of patients at risk are indicated.

FIG. 4. CAIX amino acid sequence (SEQ ID NO:1).

FIG. 5. CA9 cDNA sequence (SEQ ID NO:2).

FIG. 6A-C. CA9 genomic sequence (SEQ ID NO:3).

DETAILED DESCRIPTION OF THE INVENTION

Figure 1:
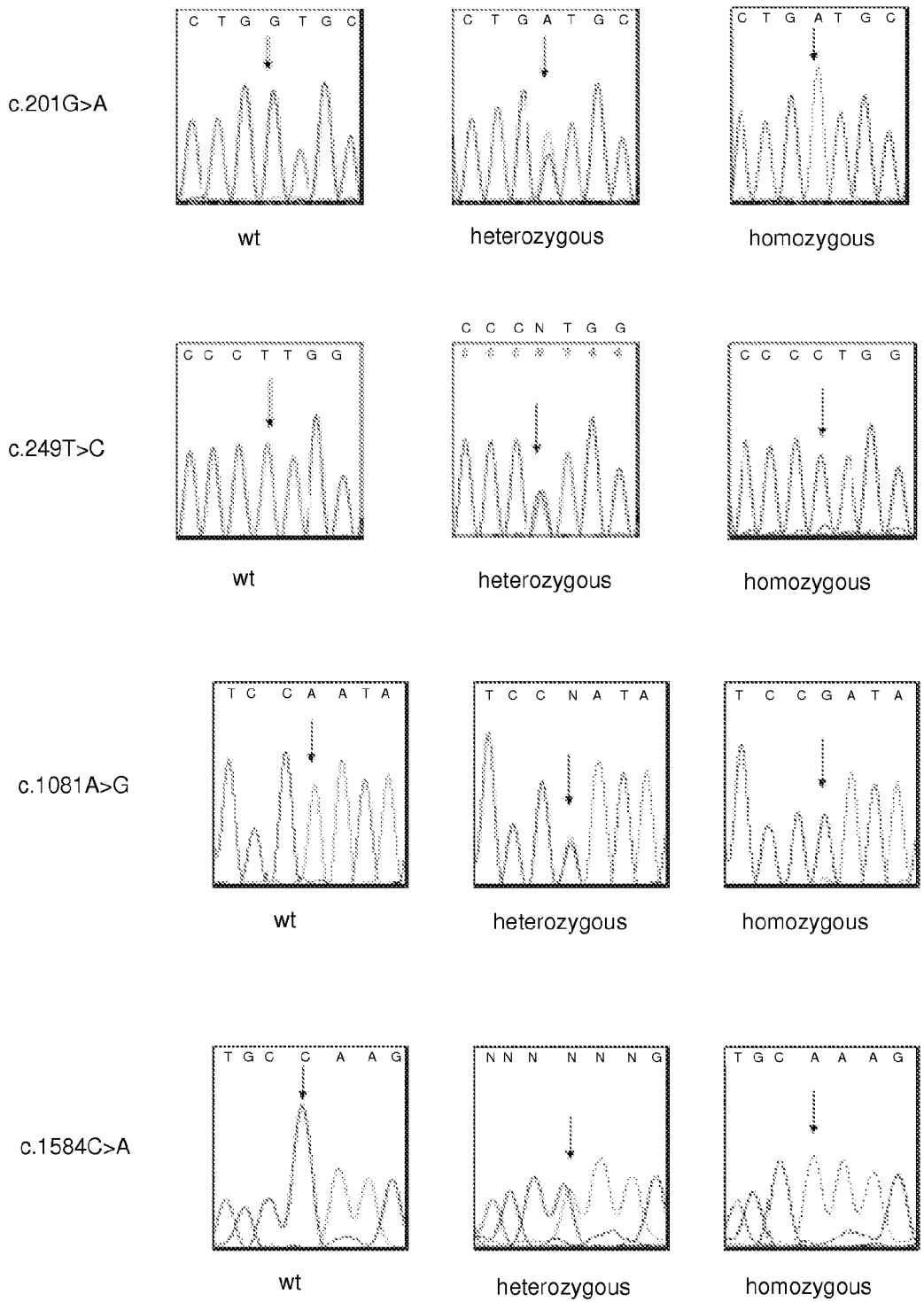
FIG. 1. Electropherograms showing wild type, heterozygous and homozygous sequences of the detected CA9 SNPs.

In its first aspect, the methods of the invention provide a prognosis for a human patient having renal cell cancer (RCC) by determining whether the patient has the SNP1 polymorphism of a nucleic acid which is identical or substantially identical to CA9 and providing the prognosis, wherein the presence of the SNP indicates a favorable prognosis and the absence of the SNP indicates a less favorable prognosis. The cancer in some further embodiments is metastatic renal cell cancer (MRCC). The determining can comprise the steps of obtaining a biological sample comprising CAIX nucleic acid from the patient and then detecting the presence of absence of the polymorphism in the nucleic acid. The nucleic acid is preferably isolated. The nucleic acid can be DNA, cDNA, mRNA, or genomic DNA. In some embodiments, the nucleic acid is amplified by PCR or other means and a T or C residue at the SNP position is detected or determined in the amplified nucleic acid. In some embodiments of any of the above, the level of expression of a CAIX protein which is identical or substantially identical to the CAIX protein of FIG. 4 (SEQ ID NO:1) is determined in a sample of cancerous tissue from the patient and if a high level of expression is found that result contributes to a favorable prognosis. Conversely a low level expression of the CAIX protein contributes to a less favorable prognosis. The prognosis can be with respect to the likelihood of surviving the cancer or the length of survival with the cancer or both. Methods of quantitating CAIX nucleic acid or protein expression and using them in providing a prognosis and/or diagnosis are taught in U.S. patent application Ser. No. 10/511,465 (assigned to the same assignee as the present application) and published as U.S. Patent Publication No. 20050158809, the contents of which are incorporated by reference in their entirety for all purposes and particularly with reference to such methods.

In other embodiments, the invention provides a method of treating a human RCC or MRCC patient by obtaining a biological sample containing CAIX nucleic acid from the patient which is identical or substantially identical to a sequence of FIG. 5 (SEQ ID NO:2) or FIG. 6 (SEQ ID NO:3) and determining as above whether the nucleic acid has the SNP1 polymorphism. Patients with the polymorphism are selected for treatment with an immunotherapy (e.g., therapy with IL-2 and/or interferon alpha). If the polymorphism is absent, the patient is treated with an alternative therapy (e.g., administration of sunitinib, sorafenib, and temsirolimus). See, de Martino et al., J Urol. 2009 August; 182(2):728-34. Epub 2009 Jun. 18) which is incorporated herein by reference in its entirety.

In a second aspect, the invention provides a composition comprising a first PCR primer which binds to DNA 3' of a site corresponding to the SNP1 polymorphism and a second PCR primer which binds to DNA 5' of the site, wherein the first and second primer are complementary to nucleic acid sequences which flank the site wherein the flanking nucleic acid sequences are each within 500, 200, 100 or 50 nucleotides of the site. In a preferred embodiment, the primers are each from 10 to 22 nucleotides in length. In another embodiment, the invention provides, a nucleic acid probe which is complementary to a CAIX nucleic acid sequence having the SNP1 polymorphism. The probe also is preferably from 12 to 22 nucleotides in length.

The invention also provides kits comprising an antibody which binds CAIX protein and a first PCR primer which binds to DNA 3' of a site corresponding to the SNP1 polymorphism and a second PCR primer which binds to DNA 5' of the site, wherein the first and second primer are complementary to nucleic acid sequences which flank the site wherein the flanking nucleic acid sequences are each within 500 nucleotides of the site; or a nucleic acid probe which is complementary to a CAIX nucleic acid sequence having the SNP1 polymorphism.

In some embodiments, the invention relates to a method of aiding in a renal cell carcinoma prognosis that includes in addition to identifying the presence or absence of a SNP in the patient also (a) quantifying expressed carbonic anhydrase IX (CAIX), if any, present in one or more samples derived from a subject diagnosed with renal cell carcinoma (e.g., renal clear cell carcinoma) to produce quantified CAIX expression data. The method also includes (b) correlating the quantified CAIX expression data with a probability of a renal cell carcinoma prognosis for the subject. The expressed CAIX typically includes a CAIX polypeptide, a fragment of a CAIX polypeptide, an mRNA that encodes a CAIX polypeptide, or the like. Although other quantification techniques are optionally utilized, in preferred embodiments, the expressed CAIX is quantified by immunohistochemical staining. In addition, the samples are generally derived from a renal tumor and/or a metastatic lesion derived from a renal tumor.

Quantified CAIX expression data correlates with various outcomes for RCC patients. For example, when the quantified CAIX expression data comprises a quantification percentage of more than 85% that quantification percentage correlates with a better prognosis for the subject than a quantification percentage of 85% or less when the subject is diagnosed with metastatic renal cell carcinoma. Further, when the quantified CAIX expression data comprises a quantification percentage of 85% or less that quantification percentage correlates with a better prognosis for the subject than a quantification percentage of 85% or less when the subject is diagnosed with non-metastatic renal cell carcinoma of T stage≥3 and Fuhrman grade≥2.

The method additionally identifies RCC patients that may benefit from particular courses of treatment. To illustrate, when the quantified CAIX expression data comprises a quantification percentage of more than 85% that quantification percentage further correlates with a likely positive response to, e.g., interleukin-2 (IL-2) immunotherapy, or one or more CAIX-targeted therapies, for the subject. In addition, when the quantified CAIX expression data comprises a quantification percentage of 85% or less that quantification percentage further correlates with a likely positive response to an adjuvant immunotherapy for the subject when the subject is diagnosed with non-metastatic renal cell carcinoma of T stage≥3 and Fuhrman grade≥2.

In another aspect, the invention relates to a method of aiding in a renal clear cell carcinoma prognosis that includes (a) quantifying expressed CAIX polypeptides, if any, present in one or more samples derived from a subject diagnosed with renal clear cell carcinoma to produce quantified CAIX polypeptide expression data in which the samples are derived from a renal tumor and/or a metastatic lesion derived from a renal tumor. The method also includes (b) correlating the quantified CAIX polypeptide expression data with a probability of a renal clear cell carcinoma prognosis in which a quantification percentage of 85% stratifies the prognosis for the subject. In preferred embodiments, the expressed CAIX polypeptides are quantified by immunohistochemical staining and the quantification percentage comprises a positive staining percentage.

The quantified CAIX expression data produced with this method also correlates with various outcomes for RCC patients and further identifies RCC patients that may need specific courses of treatment. For example, a quantification percentage of more than 85% correlates with a better prognosis for the subject than a quantification percentage of 85% or less when the subject is diagnosed with metastatic renal clear cell carcinoma, or when the subject is diagnosed with non-metastatic renal clear cell carcinoma of T stage.gtoreq.3 and Fuhrman grade.gtoreq.2. A quantification percentage of more than 85% for a sample derived from the renal tumor correlates with a lower probability of metastasis than a quantification percentage of 85% or less for the sample derived from the renal tumor. In addition, a quantification percentage of more than 85% further correlates with a likely positive response to interleukin-2 immunotherapy for the subject, or with a likely positive response to one or more CAIX-targeted therapies for the subject. Moreover, a quantification percentage of 85% or less further correlates with a likely positive response to an adjuvant immunotherapy for the subject when the subject is diagnosed with non-metastatic renal cell carcinoma of T stage≥3 and Fuhrman grade≥2.

In certain embodiments of the methods described herein, the quantified CAIX expression data are in a computer-readable form. In these embodiments, (b) typically comprises operating a programmable computer that comprises at least one database and executing an algorithm that determines closeness-of-fit between the computer-readable quantified CAIX expression data and database entries, which entries correspond to clinical and/or pathological data for a population of renal carcinoma patients (e.g., renal clear cell carcinoma patients) to thereby correlate the quantified CAIX expression data with the probability of the renal carcinoma prognosis (e.g., renal clear cell carcinoma prognosis) for the subject.

In yet another aspect, the present invention provides a computer program product comprising a computer readable medium having one or more logic instructions. The computer readable medium includes logic instructions for (a) receiving quantified CAIX expression data derived from a subject diagnosed with renal cell carcinoma. The computer readable medium also includes logic instructions for (b) determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject.

The CAIX antigen is typically quantitated in mammalian samples, which are preferably human samples. Such samples optionally include tissue specimens, body fluids (e.g., urine), tissue extracts, cells, cell lysates and cell extracts, among other samples. In preferred embodiments, samples are derived from renal tumors and/or metastatic lesions derived from renal tumors.

The CAIX antigen can be detected and quantified by various techniques. In preferred embodiments, CAIX is detected and quantified by immunohistochemical staining (e.g., using tissue arrays or the like). Preferred tissue specimens to assay by immunohistochemical staining, for example, include cell smears, histological sections from biopsied tissues or organs, and imprint preparations among other tissue samples. An exemplary immunohistochemical staining protocol is described further below. Such tissue specimens can be variously maintained, for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, percutaneous punch, and surface biopsies, among other biopsy techniques.

As mentioned, many formats for detection and quantification of the CAIX antigen are optionally adapted for use with the methods of the present invention. Certain exemplary techniques include, e.g., Western blotting, immunoassays (e.g., radioimmunoassays (RIAs), enzyme immunoassays (EIAs), etc.), immunohistochemical staining, immunoelectron and scanning microscopy using immunogold, ELISAs, competitive EIA or dual antibody sandwich assays, among other assays commonly known in the art.

Representative of one type of ELISA test for CAIX antigen is a format in which a microtiter plate is coated with antibodies made to CAIX polypeptides or antibodies made to whole cells expressing CAIX proteins, and to this is added a patient sample, for example, a tissue or cell extract. After a period of incubation permitting any antigen to bind to the antibodies, the plate is washed and another set of anti-CAIX antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance typically indicates a positive result.

It is also apparent to one skilled in the art of immunoassays that CAIX polypeptides can be used to detect and/or quantitate the presence of CAIX antigen in the body fluids, tissues and/or cells of patients. In one such embodiment, a competition immunoassay is used, wherein the CAIX protein is labeled and a body fluid is added to compete with the binding of the labeled CAIX polypeptide to antibodies specific to CAIX polypeptide.

As another exemplary embodiment, an immunometric assay may be used in which a labeled antibody made to a CAIX protein is used. In such an assay, the amount of labeled antibody which complexes with the antigen-bound antibody is directly proportional to the amount of CAIX antigen in the sample.

Antibodies suitable for use in certain embodiments of the methods described herein may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies (Glennie et al. (1982) Nature 295:712); Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions (otherwise known as the complementarity determining regions (CDRs) of the $V_H$ and $V_L$ regions); $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques (Dalbadie-McFarland et al. (1982) Proc. Natl. Acad. Sci. USA 79: 6409).

The antibodies useful according to this invention to identify CAIX polypeptides can be labeled in essentially any manner, for example, with enzymes such as horseradish peroxidase (HRP), fluorescent compounds, or with radioactive isotopes such as, $^{125}I$, among other labels.

Bispecific antibodies that are optionally adapted for use in the present invention can be produced by chemically coupling two antibodies of the desired specificity. Bispecific MAbs can preferably be developed by somatic hybridization of 2 hybridomas. Bispecific MAbs for targeting CAIX protein and another antigen can be produced by fusing a hybridoma that produces CAIX-specific MAbs with a hybridoma producing MAbs specific to another antigen. For example, a cell (a quadroma), formed by fusion of a hybridoma producing a CAIX-specific MAb and a hybridoma producing an anti-cytotoxic cell antibody, will produce hybrid antibody having specificity of the parent antibodies. See, e.g., Immunol. Rev. (1979); Cold Spring Harbor Symposium Quant. Biol., 41: 793 (1977); van Dijk et al., Int. J. Cancer, 43: 344-349 (1989). Thus, a hybridoma producing a CAIX-specific MAb can be fused with a hybridoma producing, for example, an anti-T3 antibody to yield a cell line which produces a CAIX/T3 bispecific antibody which can target cytotoxic T cells to CAIX-expressing tumor cells.

Although representative hybridomas of use in practicing this invention are formed by the fusion of murine cell lines, human/human hybridomas (Olsson et al. (1980) Proc. Natl. Acad. Sci. USA 77:5429) and human/murine hybridomas (Schlom et al. (1980) Proc. Natl. Acad. Sci. USA 77:6841; Shearman et al. (1991) J. Immunol. 146: 928-935; and Gorman et al. (1991) Proc. Natl. Acad. Sci. USA 88:4181-4185) can also be prepared among others.

Monoclonal antibodies for use in the methods of this invention may be obtained by methods well known in the art. See, e.g., Galfre and Milstein, "Preparation of Monoclonal Antibodies: Strategies and Procedures," in Methods in Enzymology: Immunochemical Techniques, 73: 1-46 [Langone and Vanatis (eds); Academic Press (1981)]. See also, Milstein and Kohler (1975) Nature 256:495-497. Monoclonal antibodies specific for this invention can be prepared by immunizing appropriate mammals, preferably rodents, rabbits or mice, with an appropriate immunogen, for example, MaTu-infected HeLa cells, CAIX fusion proteins, or CAIX proteins attached to a carrier protein, if necessary.

Representative MAbs of use in this invention include MAbs M75, MN9, MN12 and MN7. For example, Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Slovakia) and was deposited under ATCC Designation HB 11128 on Sep. 17, 1992 at the American Type Culture Collection (ATCC). The production of hybridoma VU-M75 is described in Zavada et al., International Publication No. WO 93/18152. Mab M75 recognizes both the nonglycosylated GST-MN fusion protein and native CAIX protein as expressed in CGL3 cells equally well. The M75 MAb recognizes both native and denatured forms of the CAIX protein (Pastorekova et al. (1992) Virology 187:620-626).

Antibodies employed in assays may be labeled or unlabeled. Unlabeled antibodies may be employed in agglutination; labeled antibodies may be employed in a wide variety of assays, employing a wide variety of labels known in the art. Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays (referred to above), such as radioimmunoassays, enzyme immunoassays, e.g., ELISA, fluorescent immunoassays, and the like. See, e.g., U.S. Pat. Nos. 3,766,162; 3,791,932; 3,817,837; and 4,233,402.

An exemplary immunohistochemical staining protocol using a Dako staining kit (Dako Corporation, Carpenteria, Calif.) includes dewaxing, rehydrating and blocking sample sections to remove non-specific reactivity as well as endogenous peroxidase activity. Sections can then be incubated with dilutions of the M75 monoclonal antibody. After the unbound M75 is removed by rinsing the section, the section can be sequentially reacted with a biotinylated antimouse IgG antibody and streptavidin conjugated to horseradish peroxidase; a rinsing step can be included between those two reactions and after the second reaction. Following the last rinse, the antibody-enzyme complexes can be detected by reaction with an insoluble chromogen (diaminobenzidine) and hydrogen peroxide. A positive result is indicated by the formation of an insoluble reddish-brown precipitate at the site of the primary antibody reaction. The sections can then be rinsed, counterstained with hematoxylin, dehydrated and cover slipped. Thereafter, the sections can be examined using standard light microscopy. A deposit of a reddish brown precipitate over the plasma membrane is evidence that the M75 antibody has bound to a CAIX antigen in the tissue. A known positive control (e.g., CGL3) can be stained to validate the assay. Section thickness should be taken into consideration when comparing staining intensities, as thicker sections produce greater staining intensity independent of other assay parameters.

In certain embodiments of the invention, mRNA that encodes a CAIX polypeptide is optionally detected in a sample and correlated with a prognosis for a patient. Detection of RNA transcripts may be achieved by Northern blotting, for example, in which a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography. In situ hybridization visualization may also be employed in which a radioactively labelled antisense cRNA probe is hybridized with a thin section of a biopsy sample, washed, cleaved with RNase and exposed to a sensitive emulsion for autoradiography. The samples may be stained with haematoxylon to demonstrate the histological composition of the sample, and dark field imaging with a suitable light filter illuminates the developed emulsion. Non-radioactive labels such as digoxigenin may also be used.

General texts describing additional molecular biological techniques useful herein, including the preparation of antibodies include Berger and Kimmel, Guide to Molecular Cloning Techniques, Methods in Enzymology, Vol. 152, Academic Press, Inc., Sambrook et al., Molecular Cloning—A Laboratory Manual (2nd Ed.), Vol. 1-3, Cold Spring Harbor Laboratory (1989), Current Protocols in Molecular Biology, F. M. Ausubel et al. (Eds.), Current Protocols, a joint venture between Greene Publishing Associates, Inc. and John Wiley & Sons, Inc. (supplemented through 2000), Harlow et al., Monoclonal Antibodies: A Laboratory Manual, Cold Springs Harbor Laboratory Press (1988), Paul (Ed.), Fundamental Immunology, Lippincott Williams & Wilkins (1998), and Harlow et al., Using Antibodies: A Laboratory Manual, Cold Spring Harbor Laboratory Press (1998).

Following detection and quantitation of CAIX in one or more samples from a subject diagnosed with RCC, the SNP data and CAIX expression data is correlated with clinical and/or pathological data to arrive at prognostic information for the patient. Data generated by the methods described herein is optionally analyzed using any suitable technique. Statistical analysis of data and more particularized correlations are described in greater detail in an example provided below. In one embodiment, data is analyzed with the use of a logic device, such as a programmable digital computer that is included, e.g., as part of a system. The computer generally includes a computer readable medium that stores logic instructions of the system software. Certain logic instructions are typically devoted to memory for receiving quantified CAIX expression data derived from a subject diagnosed with renal cell carcinoma. The computer also typically includes logic instructions for determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject.

In preferred embodiments, the quantified CAIX expression data is in a computer-readable form suitable for use in database queries. For example, a database query generally includes operating a programmable computer that comprises at least one database and executing an algorithm that determines closeness-of-fit between the computer-readable quantified CAIX expression data and database entries, which entries correspond to clinical and/or pathological data for a population of renal clear cell carcinoma patients to thereby correlate the quantified CAIX expression data with the probability of the renal clear cell carcinoma prognosis for the subject. In some embodiments, the algorithm includes an artificial intelligence algorithm or a heuristic learning algorithm. For example, the artificial intelligence algorithm optionally includes one or more of, e.g., a fuzzy logic instruction set, a cluster analysis instruction set, a neural network, a genetic algorithm, or the like.

The present invention also provides a computer program product comprising a computer readable medium having one or more logic instructions. The computer readable medium includes logic instructions for receiving the SNP data and (a) receiving quantified CAIX expression data derived from a subject diagnosed with renal cell carcinoma. The computer readable medium also includes logic instructions for (b) determining closeness-of-fit between the quantified CAIX expression data and database entries, which entries correspond to clinical and/or pathological data for a population of renal cell carcinoma patients to thereby correlate the quantified CAIX expression data with a probability of a renal cell carcinoma prognosis for the subject. Furthermore, the computer readable medium optionally includes, e.g., a CD-ROM, a floppy disk, a tape, a flash memory device or component, a system memory device or component, a hard drive, or a data signal embodied in a carrier wave.

In some embodiments, the presence or absence of VHL gene mutation in the cancer tissue sample is further determined to aid in the prognosis. The absence of the VHL mutation and low CAIX expression are associated with tumor aggressiveness and poor survival of clear cell renal cell carcinoma (see, Patard, et al., Int J Cancer. 2008 July; 123(2): 395-400. Both CAIX expression and VHL mutational status are able to stratify patients with clear cell RCC into distinct groups with regards to clinicopathological variables and prognosis, with low CAIX expression and absence of VHL mutation being associated with a poor clinicopathological phenotype and diminished survival. Combination of CAIX expression and VHL mutational status further enhances prognostic stratification: patients with both VHL mutation and high CAIX expression have the most favorable prognosis, patients with either VHL mutation or high CAIX expression have intermediate prognosis, and patients with neither VHL mutation nor high CAIX expression have the worst prognosis. The findings can be used for patient selection for targeted therapy. VHL alteration and inactivation through mutation or hypermethylation occurs in more than 50% of sporadic clear cell RCCs. VHL alteration is directly linked to tumorigenesis via the hypoxia-induced pathway, which leads to over-expression of several important proteins such as VEGF and CAIX.

Unless otherwise defined, all technical and scientific terms used herein have the same meaning as commonly understood by one of ordinary skill in the art to which this invention belongs.

All publications, patents, patent applications, databases and other references cited in this application are herein incorporated by reference in their entirety as if each individual publication, patent, patent application, database or other reference was specifically and individually indicated to be incorporated by reference to the extent that each is not inconsistent with the present disclosure.

As used in this specification and the appended claims, the singular forms "a," "an," and "the" include plural reference unless the context clearly dictates otherwise.

"Renal cell carcinoma" or "RCC" refers to carcinoma of the renal parenchyma. RCC is also often identified as renal cancer, "hypemephroma", or adenocarcinoma of the kidney. There are four main types of renal cell carcinoma, namely, clear cell type, granular cell type, mixed granular and clear cell type, and spindle cell type.

"Prognosis" refers to a forecast as to the probable outcome of a disease state, a determination of the prospect as to recovery from a disease as indicated by the nature and symptoms of a case, the monitoring of the disease status of a patient, the monitoring of a patient for recurrence of disease, and/or the determination of the preferred therapeutic regimen for a patient.

"Quantification percentage" refers to a CAIX expression score that includes the percentage of a sample (e.g., a target tissue or cellular sample, such as a sample from a renal tumor, a sample from a metastatic lesion derived from a metastitic lesion, and/or the like) that has positive CAIX expression. In preferred embodiments, the quantification percentage of a sample refers a CAIX expression score that includes the extent of staining or staining percentage (e.g., the percentage of cells in a sample that stain positively for CAIX, etc.). In certain embodiments, other factors such as staining intensity and the percentage staining at maximal staining intensity are also included in a CAIX expression score for a particular sample. For example, as illustrated in an example provided below, survival tree analysis of CAIX scoring information from the analyzed tissue arrays identified that a staining percentage of 85% was an ideal cutoff for stratification for patient survival. Staining percentages>85%, irrespective of intensity, were considered high CAIX staining, whereas those .ltoreq.85% were considered low CAIX staining As used herein nucleic acid, polynucleotide and oligonucleotide are used interchangeably and refer to a polymeric (e.g., 2 or more monomers) of nucleotides of any length. A nucleic acid can be DNA, RNA, mRNA, or cDNA, and be single- or double-stranded. Oligonucleotides can be naturally occurring nucleotides or synthetic nucleotides, but are typically prepared by synthetic means. Preferred nucleic acids of the invention include segments of DNA or their complements including a nucleotide having a sequence identical or completely complementary to the sequence of SEQ ID NO: 2 or 3 about the SNP1 site or including sequences identical or completely complementary to a sequence of SEQ ID NO:2 or 3 in which the sequences includes the position of a SNP or a SNP set forth therein (e.g., SNP1). The segments are usually between 10 and 100 contiguous bases, and often range from about 12 to 30, 15 to 30, or 20 to 30 nucleotides or from about 20 to about 50 nucleotides. The nucleic acid bases are typically selected from G, C, T, U, and A. Some nucleic acids contain one or a plurality of polymorphic sites and have one, or two or more polymorphic sites.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon).

For full-length genes and entire protein-coding sequences, a SNP flanking sequence can be, for example, up to about 3 KB, 2 KB, 1 KB on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from flanking sequences of appropriate length such that it can be subjected to the specific manipulations or uses described herein such as preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Polymorphs are set forth in Table 3. Furthermore, fragments of such full-length genes and transcripts that contain one or more SNPs disclosed herein are also encompassed by the present invention, and such fragments may be used, for example, to express any part of a protein, such as a particular functional domain or an antigenic epitope.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Polymorphs are set forth in Table 3. Furthermore, fragments of such full-length genes and transcripts that contain one or more SNPs disclosed herein are also encompassed by the present invention, and such fragments may be used, for example, to express any part of a protein, such as a particular functional domain or an antigenic epitope.

Thus, the present invention also encompasses fragments of the nucleic acid sequences. A fragment typically comprises a contiguous nucleotide sequence at least about 8 or more nucleotides, more preferably at least about 12 or more nucleotides, and even more preferably at least about 16 or more nucleotides. Further, a fragment could comprise at least about 18, 20, 22, 25, 30, 40, 50, 60, 80, 100, 150, 200, 250 or 500 (or any other number in-between) nucleotides in length. The length of the fragment will be based on its intended use as a polynucleotide probe or primer. A labeled probe can then be used, for example, to screen a cDNA library, genomic DNA library, or mRNA to isolate nucleic acid corresponding to the coding region. Further, primers can be used in amplification reactions, such as for purposes of assaying one or more SNPs sites or for cloning specific regions of a CAIX gene.

An isolated nucleic acid molecule of the present invention further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). Based on such methodologies, a person skilled in the art can readily design primers in any suitable regions 5' and 3' to a SNP disclosed herein. Such primers may be used to amplify DNA of any length so long that it contains the SNP of interest in its sequence.

As used herein, an "amplified polynucleotide" of the invention is a SNP-containing nucleic acid molecule whose amount has been increased at least five-fold by any nucleic acid amplification method performed in vitro as compared to its starting amount in a test sample. In other preferred embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, 300, 400, or 500 nucleotides in length. While the total length of an amplified polynucleotide of the invention can be as long as an exon, an intron or the entire gene where the SNP of interest resides, an amplified product can be up to about 1,000 nucleotides in length (although certain amplification methods may generate amplified products greater than 1000 nucleotides in length). More preferably, an amplified polynucleotide is not greater than about 600-700 nucleotides in length. It is understood that irrespective of the length of an amplified polynucleotide, a SNP of interest may be located anywhere along its sequence.

In a specific embodiment of the invention, the amplified product contains a SNP disclosed herein (e.g., SNP1).

The present invention provides isolated nucleic acid molecules that comprise, consist of, or consist essentially of one or more polynucleotide sequences that contain one or more SNPs disclosed herein, complements thereof, and SNP-containing fragments thereof.

Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications, for example, those with uncharged linkages (e.g., methyl phosphonates, phosphotriesters, phosphoamidates, carbamates, etc.), those containing pendant moieties, including, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

Sequence means the linear order in which monomers occur in a polymer, for example, the order of amino acids in a polypeptide or the order of nucleotides in a polynucleotide.

A complementary nucleotide sequence is one which allows binding to the reference nucleotide sequence in a sequence specific manner under stringent conditions. A complementary sequence is usually at least 90%, 95%, 96%, 97%, 98%, or 99% identical (or completely identical) to a referenced sequence. Complementary sequences include completely complementary sequences as determined by application of the Watson-Crick base pairing rules such that the bases G, A, and T of the first nucleic acid are respectively and consistently paired with the bases C, U, and A of the second or reference nucleic acid (e.g., 5'-A-G-T-C-3' base pairs with 3'-T-C-A-G-5').

As used herein, the term isolated, refers to a nucleic acid or polypeptide which is separated from other nucleic acid molecules, polypeptides, or cellular materials when such were present in the source of the nucleic acid molecule or polypeptide. An "isolated" nucleic acid molecule, for example, a cDNA molecule, can be substantially free of other cellular material, or culture medium when produced by recombinant techniques, or substantially free of chemical precursors or other chemicals when chemically synthesized. An isolated entity is removed typically from at least a majority of the differing constituents of the source as evaluated by total mass of the differing constituents in a medium. In other words, it is typically has at most one-half, one-fourth or one-eighth the total contaminants as the source material. In a preferred embodiment, a nucleic acid molecule encoding a single nucleotide polymorphism of the invention or including the position of a single nucleotide polymorphism of the invention is isolated. In another preferred embodiment, the SNP of the isolated nucleotide is SNP1.

"SNP" refers to a single nucleotide polymorphism in a gene sequence. The SNP can occur in any region of the gene, including the promoter region, untranslated 5' and 3' regions, introns, and coding regions found in the mRNA. Single nucleotide polymorphism (SNP) analysis is useful for detecting differences between alleles of the CAIX polynucleotides (e.g., genes) of the invention.

"CAIX or CA9" with reference to nucleic acids, e.g., gene, pre-mRNA, mRNA, and polymorphic variants, alleles, mutants concerns human nucleic acid sequences having greater than about 95%, preferably greater than about 96%, 97%, 98%, 99%, or higher nucleotide sequence identity, preferably over a region of at least about 25, 50, 100, 150, 200, 250, 500, 1000, or more nucleotides, to the referenced nucleic acid sequence (e.g., SEQ ID NOS:2 and 3). The sequence may differ only be a referenced SNP or a combination of the SNPs disclosed herein.

"Nucleic acid" refers to polymers of deoxyribonucleotides and ribonucleotides in either single- or double-stranded form, and the complements thereof. In the context of primers and probes, the term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

"CAIX or CA9" with reference to polypeptides and proteins concerns human polypeptides having an amino acid sequence that has greater than about 90% amino acid sequence identity, preferably 91%, 92%, 93%, 94%, 95%, 96%, 97%, 98% or 99% or greater amino acid sequence identity, preferably over a region of over a region of at least about 25, 50, 100, 200, 500, or more amino acids, to a polypeptide encoded by a referenced CAIX nucleic acid or an amino acid sequence described herein, for example, as depicted in SEQ ID NO:1. The nucleic acids and proteins of the invention include both isolated and recombinant molecules.

The terms "polypeptide," "peptide" and "protein" are used interchangeably herein to refer to a polymer of amino acid residues. The term "amino acid" refers to naturally occurring. Naturally occurring amino acids are those encoded by the genetic code, as well as those amino acids that are later modified, e.g., hydroxyproline, y-carboxyglutamate, and O-phosphoserine. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Linkage disequilibrium or allelic association denotes a preferential association of a particular allele or genetic marker with a specific allele, or genetic marker at a nearby chromosomal location more frequently than expected by chance for the particular allelic frequencies in the population. To illustrate, let locus A have alleles $a_1$ and $a_2$, which occur equally frequently. Let A be linked to locus B having alleles $b_1$ and $b_2$, which occur equally frequently. The haplotype $a_{1b1}$ ought to have a frequency of 0.25 in the population. If $a_{1b1}$ occurs more frequently, then alleles $a_1$ and $b_1$ are in linkage disequilibrium. Linkage disequilibrium may result from natural selection or because an allele is too new to have achieved equilibrium with the linked allele.

Linkage disequilibrium markers can be used to detect a trait even when the marker itself does not cause the trait. To illustrate, a marker (A) that is not a cause of a trait, but which is in linkage disequilibrium with a gene (B) causing the trait, can be used to detect a trait to indicate susceptibility to the trait even when the gene A may not have been identified or detected. Newer alleles (i.e., arising from mutation relatively recently) are expected to have a larger genomic sequence-ment in linkage disequilibrium. The age of an allele can be determined by comparing its occurrence between ethnic human groups and/or between humans and related species.

Hybridization probes capable of binding in a base-specific manner to a SNP site of a completely complementary strand of nucleic acid are also provided by the invention. Such probes include nucleic acids and peptide nucleic acids, as described in Nielsen et al., Science 254, 1497-1500 (1991). Hybridizations are usually performed under stringent hybridization conditions. Stringent hybridization conditions typically refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents (e.g., formamide). For selective or specific hybridization, a positive signal is at least two times background, preferably 10 times background hybridization.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Biological sample" is used in its broadest sense to reference samples from a patient containing CAIX nucleic acid or protein. They sample may comprise a bodily fluid including, but not limited to, ascites, blood, serum, plasma, platelets, saliva, cerebrospinal fluid, lymph, semen, sputum, urine and the like; the soluble fraction of a cell preparation, or an aliquot of media in which cells were grown; a chromosome, an organelle, or membrane isolated or extracted from a cell; genomic DNA, mRNA, or cDNA in solution or bound to a substrate; a cell; a tissue patient tissue, (e.g., sections of tissues such as cancer biopsy samples, frozen sections taken for histologic purposes), a tissue biopsy, or a tissue print; buccal cells, skin, hair, a hair follicle; and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

The increased likelihood of an individual having a trait (responder/non responder to a therapy or favorable/unfavorable outcome with respect to survival) is with reference to a population of individuals who do not harbor the polymorphic form associated with the likelihood of having the trait. Generally, the increased likelihood can be assessed in terms of an odds ratio which compares the frequency of a polymorphism in a population having a trait to a well-matched control population not having the trait. Odds ratios that are greater than 1 are generally indicative of a trait being associated with a polymorphism. The greater the odds ratio, the greater the risk. In some embodiments, the SNP is associated with odds ratios of at least 1.4, 1.5, 1.8, 2, 3, or 5 for an inflammatory disorder, immune system disorder or a cell proliferation disorder. Such SNPs can be particularly useful in assessing the risk of developing such a disorder or the increased likelihood of a person having a SNP responding therapeutic or prophylactic treatment.

To amplify a target SNP, the nucleic acid encoding the SNP is made accessible to the components of the amplification system. In general, this accessibility is ensured by isolating the nucleic acids from the sample, however, isolation is optional (methods for amplifying nucleic acids, e.g., by PCR from whole cells are known and appropriate). A variety of techniques for extracting nucleic acids from biological samples are known in the art. For example, see those described in Rotbart et al., 1989, in PCR Technology (Erlich ed., Stockton Press, New York) and Han et al., 1987, Biochemistry 26:1617-1625. The methods described by Fries et al., Am. J. Med. Genet., 46:363-368 (1993), are also useful.

Nucleic acids are isolated from biological samples from patients, and from cell culture. The culture of cells used in conjunction with the present invention, including cell lines and cultured cells from tissue or blood samples, including stem cells is well known in the art. Freshney (Culture of Animal Cells, a Manual of Basic Technique, third edition Wiley-Liss, New York (1994)) and the references cited therein provides a general guide to the culture of cells. See also, Kuchler et al. (1977) Biochemical Methods in Cell Culture and Virology, Kuchler, R. J., Dowden, Hutchinson and Ross, Inc, and Inaba et al. (1992) J. Exp. Med. 176, 1693-1702.

When the sample contains a small number of cells, extraction may be accomplished, e.g., by methods as described in Higuchi, "Simple and Rapid Preparation of Samples for PCR", in PCR Technology, Ehrlich, H. A. (ed.), Stockton Press, New York, which is incorporated herein by reference.

A relatively easy procedure for extracting DNA for amplification is a "salting out" procedure adapted from the method described by Miller et al., Nucleic Acids Res., 16:1215 (1988)

Kits are also commercially available for the extraction of high-molecular weight (i.e., genomic) DNA. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA when practicing the methods of the present invention.

The nucleic acids embracing the SNPs are typically amplified when determining whether a SNP is present in a sample. In a preferred embodiment, amplification is performed by the PCR method. The PCR process is well known in the art (see, U.S. Pat. Nos. 4,683,195; 4,683,202; and 4,965,188. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology 43:63-67; and Radding, 1982, Ann. Rev. Genetics 16:405-436, both of which are incorporated herein by reference).

Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In some instances, SNP-encoding RNA may be used as the initial template for primer extension is RNA. Polymerizing agents suitable for synthesizing a complementary, DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Roche Molecular Systems. When RNA is amplified, an initial reverse transcription (RT) step is carried out to create a DNA copy (cDNA) of the RNA. PCT patent publication No. WO 91/09944, published Jul. 11, 1991, incorporated herein by reference, describes high-temperature reverse transcription by a thermostable polymerase that also functions in PCR amplification. High-temperature RT provides greater primer specificity and improved efficiency. A "homogeneous RT-PCR" in which the same primers and polymerase suffice for both the reverse transcription and the PCR amplification steps, and the reaction conditions are optimized so that both reactions occur without a change of reagents is also available. *Thermus thermophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

Those skilled in the art will know that the PCR process is most usually carried out as an automated process with a thermostable enzyme. In this process, the temperature of the reaction mixture is cycled through a denaturing region, a primer annealing region, and an extension reaction region. Alternatively, the annealing and extension temperature can be the same. Reverse transcriptase-PCR uses such a two-step temperature cycling. A machine specifically adapted for use with a thermostable enzyme is commercially available from Roche Molecular Systems.

Those practicing the present invention should note that, although the preferred embodiment incorporates PCR amplification, amplification of target sequences it a sample may be accomplished by any known method, such as ligase chain reaction (LCR), transcription amplification, and self-sustained sequence replication, each of which provides sufficient amplification so that the target sequence can be detected by nucleic acid hybridization to a probe. Persons of skill will appreciate that in methods such as LCR, primers that are complementary to the specific polymorphism or mutation are used. In this instance amplification occurs when the polymorphism (i.e., point mutation) is present in the nucleic acid sample.

Alternatively, methods that amplify the probe to detectable levels can be used, such as replicase amplification. The term "probe" encompasses, inter alia, the sequence specific oligonucleotides used in the above procedures; for instance, the two or more oligonucleotides used in LCR are "probes" for purposes of the present invention, even though some embodiments of LCR only require ligation of the probes to indicate the presence of an allele.

Examples of techniques sufficient to direct persons of skill through such in vitro amplification methods, including the polymerase chain reaction (PCR) the ligase chain reaction (LCR), Q.beta.-replicase amplification and other RNA polymerase mediated techniques (e.g., NASBA) are found in Berger and Kimmel, Guide to Molecular Cloning Techniques, Methods in Enzymology volume 152 Academic Press, Inc., San Diego, Calif. (Berger); Sambrook at al. (1989) Molecular Cloning—A Laboratory Manual (2nd ed.) Vol. 1-3, Cold Spring Harbor Laboratory, Cold Spring Harbor Press, NY, (Sambrook); and Current Protocols in Molecular Biology, F. M. Ausubel et al., ads., Current Protocols, a joint venture between Greene Publishing Associates, Inc. and John Wiley & Sons, Inc., (1994 Supplement) (Ausubel), and in Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36-47; The Journal Of NIH Research (1991) 3, 81-94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem.

35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039.

The present invention provides, inter alia, a polymorphic forms of CAIX9. The polymorphisms can be detected by a variety of amplification techniques, preferably PCR as described supra. To detect a polymorphism by PCR, the PCR reaction is performed in the presence of primers that are complimentary to opposite strands of the genomic DNA, wherein the complementary sequences are located on either side of the point mutation. The precise sequences recognized by the primers are not critical. Typically, any pair of primers can be used as long as they (1) bracket the polymorphism, (2) are reasonably near to the polymorphism (while the primer binding sequence may be as far from the polymorphism as can support a PCR reaction, i.e., 1 to about 10 kb, it is preferable that the binding sequence be within about 500 nucleotides or less, and more preferable that the binding sequence be within 100 nucleotides of the SNP site to be assayed), and (3) bind the primers with an adequate degree of specificity. It is preferable that the sequence be unique to the gene of interest. Such sequences are identified by comparing sequences as described herein. Smaller primers have a higher probability of recognizing sites outside of the desired binding site, whereas very large primers are more expensive to make; generally, a primer of about 15-20 nucleotides is adequate, and therefore preferred.

Exemplary primers used herein are found in Table 1.

The present invention also provides kits for the detection of genetic polymorphisms or mutations associated with the disclosed SNPs. The kits comprise a vial containing amplification primers that span a SNP. The kits optionally contain a vial containing a thermostable polymerase, genetic size markers for gels, amplification reagents, instructions and the like. The kit may also contain antibodies specific for CAIX protein.

A variety of methods can be employed to analyze the nucleotide sequence of the amplification products. Several techniques for detecting point mutations following amplification by PCR have been described in Chehab et al., Methods in Enzymology, 216:135-143 (1992); Maggio et al., Blood, 81(1):239-242 (1993); Cai and Kan, Journal of Clinical Investigation, 85(2):550-553 (1990) and Cai et al., Blood, 73:372-374 (1989).

One particularly useful technique is analysis of restriction enzyme sites following amplification. In this method, amplified nucleic acid segments are subjected to digestion by restriction enzymes. Identification of differences in restriction enzyme digestion between corresponding amplified segments in different individuals identifies a point mutation. Differences in the restriction enzyme digestion is commonly determined by measuring the size of restriction fragments by electrophoresis and observing differences in the electrophoretic patterns. Generally, the sizes of the restriction fragments is determined by standard gel electrophoresis techniques as described in Sambrook, and, e.g., in Polymeropoulos et al., Genomics, 12:492-496 (1992).

Another useful method of identifying point mutations in PCR amplification products employs oligonucleotide probes specific for different sequences. The oligonucleotide probes are mixed with amplification products under hybridization conditions. Probes are either RNA or DNA oligonucleotides and optionally contain not only naturally occurring nucleotides but also analogs such as digoxygenin dCTP, biotin dCTP, 7-azaguanosine, azidothymidine, inosine, or uridine. The advantage of using nucleic acids comprising analogs include selective stability, resistance to nuclease activity, ease of signal attachment, increased protection from extraneous contamination and an increased number of probe-specific colored labels. For instance, in preferred embodiments, oligonucleotide arrays are used for the detection of specific point mutations as described below.

Probes are typically derived from cloned nucleic acids, or are synthesized chemically. When cloned, the isolated nucleic acid fragments are typically inserted into a replication vector, such as lambda phage, pBR322, M13, pJB8, c2RB, pcos1EMBL, or vectors containing the SP6 or 17 promoter and cloned as a library in a bacterial host. General probe cloning procedures are described in Arrand J. E., Nucleic Acid Hybridization A Practical Approach, Hames B. D., Higgins, S. J., Eds., IRL Press 1985, pp. 17-45 and Sambrook, J., Fritsch, E. F., Maniatis, T., Molecular Cloning A Laboratory Manual, Cold Spring Harbor Press, 1989, pp. 2.1-3.58, both of which are incorporated herein by reference.

Oligonucleotide probes and primers are synthesized chemically with or without fluorochromes, chemically active groups on nucleotides, or labeling enzymes using commercially available methods and devices like the Model 380B DNA synthesizer from Applied Biosystems, Foster City, Calif., using reagents supplied by the same company. Oligonucleotides for use as probes, e.g., in in vitro amplification methods, or for use as gene probes are typically synthesized chemically according to the solid phase phosphoramidite triester method described by Beaucage and Caruthers (1981), Tetrahedron Letts., 22(20):1859-1862, e.g., using an automated synthesizer, as described in Needham-VanDevanter et al. (1984) Nucleic Acids Res., 12:6159-6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) J. Chrom. 255:137-149. The sequence of the synthetic oligonucleotides can be verified using the chemical degradation method of Maxam and Gilbert (1980) in Grossman and Moldave (eds.) Academic Press, New York, Methods in Enzymology 65:499-560.

Oligonucleotide probes and primers are selected using commercially available computer programs to compare known DNA sequences from gene sequences found in gene libraries, such as Genebank and EMBL, and the sequences described herein. The programs identify unique nucleotide sequences within the gene of interest. One such program is Eugene. Oligonucleotide sequences for PCR of a unique genomic DNA such as a chromosome subsequence are chosen optimally by choosing sequences according to previously established protocols or by computer programs that choose the degree of homology desired along with the length of the probe. Sequences are chosen to avoid technical problems such as primer dimers resulting from amplification of hybridized primers.

Primers and probes are optionally labeled with fluorophores or enzymes that generate colored products. This allows simultaneous use of probes to different DPDD-related polymorphisms or mutations. Identification of hybridization of a specifically labelled primer provides a means for determining which polymorphism or mutation is present in the nucleic acid of the sample. The primers used in the assay are labeled with more than one distinguishable fluorescent or pigment color. Primers are labeled with Texas red, rhodamine and its derivatives, fluorescein and its derivatives, dansyl, umbelliferone and the like or with horse radish peroxidase, alkaline phosphatase, biotin, avidin, or the like.

Primers and probes are labeled directly or indirectly. The common indirect labeling schemes covalently bind a ligand to the nucleotide and prepare labeled probe by incorporating the ligand using random priming or nick translation. The ligand then binds an ant-ligand which is covalently bound to a label. Ligands and anti-ligands vary widely. When a ligand has an anti-ligand, e.g., biotin, thyroxine, or cortisol, the ligand is used in conjunction with the labelled naturally-occurring anti-ligand. Alternatively, a hapten or antigen may be used in combination with an antibody, which is optionally labeled.

Sequence specific oligonucleotide probes hybridize specifically with a particular segment of the target polymorphism or mutation amplification products and have destabilizing mismatches with the sequences from other polymorphisms or mutations. Under sufficiently stringent hybridization conditions, the probes hybridize specifically only to exactly complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related polymorphisms or mutations.

Specific CAIX polymorphisms or mutations are also identified by sequencing the amplification products or restriction fragments thereof. Sequencing is performed by a variety of methods well known in the art. For example, the sequence of the amplified nucleic acid segments may be determined by the Maxam-Gilbert chemical degradation method as described in Sambrook. Generally, Sanger dideoxy-mediated sequencing is employed as described in Sambrook, or sequencing by hybridization is performed as described below.

In one preferred class of embodiments, the SNP is detected by hybridization of amplification products which include the splicing site to oligonucleotide arrays which discriminate single base-pair mismatches. In this embodiment, primers are used to amplify a SNP in a PCR reaction, resulting in PCR amplicons which comprise the SNP. The sequence of the entire PCR amplicon, or any subsequence thereof can be determined by labeling the PCR amplicon (typically with biotin or a fluorescent label) and hybridization to an array of oligonucleotide probes. In these hybridization methods single base pair mismatches in labeled nucleic acids to probes in the array are distinguished.

Preferably in this class of embodiments, the oligonucleotide arrays are designed to sequence nucleic acids at the SNP. More preferably, the arrays are designed to discriminate whether a particular nucleotide is altered relative to the wild-type sequence. This is done by constructing an array with two or more oligonucleotide probe sets which differ by a single nucleotide. Hybridization to the known probe sequence by a target nucleic acid under conditions where a single mismatch does not bind indicates the presence of a fully complementary nucleic acid.

Sequencing by hybridization to arrays of oligonucleotides is described in U.S. Pat. No. 5,202,231, to Drmanac et al. and, e.g., in Drmanac et al. (1989) Genomics 4:114-128. Methods of constructing and designing arrays for sequencing and detection of single nucleotide alterations is known in the art. The development of very large scale immobilized polymer synthesis (VLSIPS™) technology provides methods for arranging large numbers of oligonucleotide probes for the detection and sequencing of nucleic acids in very small arrays. See, WO 90/15070 and 92/10092; Pirrung et al., U.S. Pat. No. 5,143,854 (see also PCT Application No. WO 90/15070); McGall et al., U.S. Pat. No. 5,412,087; and U.S. Pat. No. 5,384,261. See also, Fodor et al. (1991) Science, 251: 767-777 and Sheldon et al. (1993) Clinical Chemistry 39(4): 718-719. The oligonucleotide arrays are typically placed on a solid surface such as a glass slide with an area less than 1 inch squared, although much larger surfaces are optionally used.

Mechanical and light directed oligonucleotide array construction methods are used for the construction of oligonucleotide arrays. Light directed methods are the most common, and are found, e.g., in U.S. Pat. No. 5,143,854. The light directed methods discussed in the '854 patent typically proceed by activating predefined regions of a substrate or solid support and then contacting the substrate with a preselected monomer solution. The predefined regions are activated with a light source, typically shown through a photolithographic mask. Other regions of the substrate remain inactive because they are blocked by the mask from illumination. Thus, a light pattern defines which regions of the substrate react with a given nucleic acid reagent. By repeatedly activating different sets of predefined regions and contacting different reagent solutions with the substrate, a diverse array of oligonucleotides is produced on the substrate. Other steps, such as washing unreacted reagent solutions from the substrate, are used as necessary.

The surface of a solid support is typically modified with linking groups having photolabile protecting groups and illuminated through a photolithographic mask, yielding reactive hydroxyl groups in the illuminated regions. For instance, during oligonucleotide synthesis, a 3'-O-phosphoramidite (or other nucleic acid synthesis reagent) activated deoxynucleoside (protected at the 5'-hydroxyl with a photolabile group) is then presented to the surface and coupling occurs at sites that were exposed to light in the previous step. Following capping, and oxidation, the substrate is rinsed and the surface illuminated through a second mask, to expose additional hydroxyl groups for coupling. A second 5'-protected, 3'O-phosphoramidite activated deoxynucleoside (or other monomer as appropriate) is then presented to the resulting array. The selective photodeprotection and coupling cycles are repeated until the desired set of oligonucleotides (or other polymers) is produced.

The PCR amplicons detected on the arrays are labeled with a composition detectable by spectroscopic, photochemical, biochemical, immunochemical, or chemical means. For example, useful labels include $^{32}P$, $^{35}S$, fluorescent dyes, chromophores, electron-dense reagents, enzymes (e.g., as commonly used in an ELISA), biotin, dioxigenin, or haptens and proteins for which antisera or monoclonal antibodies are available. In preferred embodiments, the label is detectable spectroscopically, i.e., is chromogenic. Suitable chromogens include molecules and compounds which absorb light in a distinctive range of wavelengths so that a color may be observed, or emit light when irradiated with radiation of a particular wavelength or wavelength range (e.g., a fluorescent label).

EXAMPLES

Methods of immunotherapy using IL-2 and/or interferon alpha are also known in the art. (see, Fyfe et al., Journal of Clinical Oncology, Vol 13, 688-696 (1995) and Rosenberg et al., Annalso of Surgery, Vol. 228, No. 3, 307-319 (1998) which are incorporated herein by reference.

In all the above aspects and embodiments of the invention having SNP subject matter, in some embodiments, the SNP is preferably SNP1 (rs12553173 (c.249T>C)).

The following examples are offered by way of illustration and not limitation. One of skill will readily recognize a variety of parameters and conditions which can be changed or modified to yield essentially identical results.

The Applicants assessed the frequency of Carbonic Anhydrase 9 (CA9) single nucleotide polymorphisms (SNPs) and mutations and their association with CAIX protein expression, response to IL-2 and overall survival in 54 Caucasian patients with metastatic clear cell renal cell carcinoma (MRCC). Genomic DNA was extracted from frozen tumor samples. Seven amplimers covering the whole coding sequence of the CA9 gene were synthesized by PCR and sequenced. The monoclonal antibody M75 was used to evaluate CAIX protein expression immunohistochemically. Associations of SNPs with clinicopathological variables and CAIX expression were assessed with Fisher's Exact tests and Kruskal-Wallis tests, respectively. CA9 reference SNP (rs) 2071676 was found in 59%, rs12553173 in 15%, rs3829078 in 11% and rs1048638 in 33% of the patients. The deletion c.376del393 was observed in two patients. CAIX expression was high (>85%) in 65% and low in 35% of patients. None of the SNPs was associated with CAIX expression, but a trend was observed for the presence of a SNP at rs12553173 (high CAIX: 88% vs. 61%, p=0.145). Patients with the C allele variant of rs12553173 had improved overall survival compared to those without (median survival: 27.3 vs. 13.6 months, p=0.0431) and a greater likelihood of response to IL-2 (57% vs. 22%, p=0.081) No other SNPs was associated with overall survival or response to IL-2. Likewise, high CAIX expression was associated with longer median survival (25.5 vs. 8.5 months, p<0.0001) and a greater IL-2 response rate (37% vs. 8%, p=0.070). In a multivariate Cox proportional hazards model, both C allele variant of CA9 SNP rs12553173 and CAIX expression were retained as independent prognostic factors of overall survival. The details of this work are next provided.

Patients and Methods

The study included 54 consecutive Caucasian patients, who underwent radical nephrectomy with regional lymph node dissection for sporadic, unilateral, clear cell MRCC. Only Caucasian patients were chosen for the study, since the frequencies of CA9 SNPs differ among the races and race has been shown to be a prognostic indicator for MRCC [24]. Moreover, only patients with clear cell MRCC were included, since CAIX is most significantly associated with the pathobiology and prognosis in this subtype [25, 26].

Age, gender, ECOG performance status [27], 2002 T, N, and M stage [28], and overall survival were collected for each case. Hematoxylin & Eosin (H&E) slides were reviewed by one anatomical pathologist (DS) to confirm the histological subtype and to re-grade tumors according to Fuhrman criteria [29]. The study protocol was approved by the institutional review board.

Genomic DNA was extracted from 50 mg frozen tissue sections using QIAamp DNA minikit (Qiagen Inc., Valencia, Calif.). DNA quantity and quality were estimated by optical density (OD 260/280) measurement and 0.8% agarose gel electrophoresis using standard protocols.

All eleven CA9 exons and flanking intronic regions were PCR amplified by specific primer pairs (Table 1). We amplified 50 to 150 ng of tumor DNA in 50 μA, with a final $MgCl_2$ specific for each amplification, 100 ng of template DNA, 1× reaction buffer, 0.2 mM of each nucleotide, 30 μmol of primers and 0.3 U of DNA polymerase (Platinum Taq, Invitrogen, Carlsbad, Calif.). PCR reactions were carried out for 35 cycles with denaturation at 94° C. for 1 min, annealing at 60° C. for 1 min and extension at 72° C. for 1 min. Forward and reverse automatic sequencing was performed using BigDye Terminator v1.1 Cycling Sequencing kit on a 3730 DNA Analyzer (Applied Biosystems, Foster City, Calif.). All SNPs and mutations were confirmed in a second round of PCR and sequencing reactions.

CAIX Protein Expression

CAIX protein expression of the primary tumor was evaluated by immunohistochemistry using the tissue microarray technique, as described previously [25]. In brief, three core tissue biopsies of the tumor and one core tissue biopsy from normal renal tissue were taken from each paraffin-embedded specimens and precisely arrayed using a custom-built instrument [30]. A Dako Envision staining system (Dako, Carpinteria, Calif.) and the mouse monoclonal antibody MN75 at a 1:10,000 dilution (a gift from Dr. Eric Stanbridge, University of California-Irvine) were used for the staining Semi-quantitative assessment of CAIX staining was performed by one anatomical pathologist (DS) blinded to pathological variables, CA9 status and survival. Expression was evaluated as the percentage of the entire tumor sample that stained positive for CAIX.

Analyses were all performed using R v2.4. Associations of SNPs with clinicopathological variables and CAIX expression were assessed with Fisher's Exact tests and Kruskal-Wallis tests, respectively. Kaplan-Meier curves were generated to estimate the overall survivor functions, which were compared using log-rank tests. A multivariate Cox proportional hazards regression model was fit to identify factors independently associated with overall survival.

Results

Patient Population

There were 42 men (78%) and 12 women (22%), who were diagnosed with clear cell MRCC with a median age of 64 years (range 34-78). An ECOG PS of >1 was assigned to 41 patients (76%). Pathological examination showed a T1, T2, T3, and T4 tumor in 7 (13%), (9%), 36 (67%), and 6 (11%) patients, respectively. Involvement of the regional nodes (N+) was observed in 14 patients (26%). Fifty percent of the tumors were high grade (Grade 3 or 4).

CA9 SNPs

Sequencing of CA9 in our patients showed SNPs in exon 1, exon 7 and the 3' UTR region, while all other nine exons had wild type sequences (Table 2, Table 3). Most SNPs were noted in exon 1. On position 201 of the cDNA, guanine was replaced with adenine (c.201G>A), referring to reference SNP (rs)2071676 of the SNP NCBI database (http://www.ncbi.nlm.nih.gov/SNP/snp reficgi?rs=2071676). A SNP at rs2071676 was seen in 32 tumors (59%), of which 21 were heterozygous and 11 homozygous. The second most frequent variant was the synonymous SNP rs12553173 (c.249T>C), which was detected in 8 tumors (15%; 7 heterozygous, 1 homozygous). In exon 7, we noted the SNP rs3829078 (c.1081A>G) in 6 cases (5 heterozygous, 1 homozygous). The SNP rs1048638 (c.1584C>A), located in the non-coding 3' UTR flanking region, was observed in 18 cases (33%), of which 16 were heterozygous and 2 homozygous. Interestingly, all cases with rs1048638 had the wild type sequence for rs3829078. All 11 patients with homozygous rs2071676 had the wild type sequence for rs12553173. CA9 SNPs, frequency, positions, function, and subsequent amino acid changes are summarized in Table 3. In addition to SNPs, we observed the novel deletion c.376del393 in two patients.

CAIX Protein Expression

CAIX staining was seen in 52 of the 54 tumors (96%), and was not observed in normal renal tissue as previously described. Using the 85% expression cut-point defined by Bui et al. [25], expression was considered high (>85%) in 35 tumors (65%) and low (<85%) in 19 tumors (35%).

None of the SNPs were significantly associated with CAIX expression. However, a trend was observed for the SNP rs12553173 (c.249T>C): 88% of the tumors with rs12553173 showed high CAIX expression in contrast to only 61% of tumors with the wild type sequence at this location. However, due to small sample size, this difference did not quite reach statistical significance (p=0.145). Likewise, CAIX expression was higher when expression levels were assessed as a continuous variable (mean expression±SE: 88.2±11.7% vs. 78.1±4.9%, p=0.100).

Association with Overall Survival and Response to IL-2

At the time of analysis, 49 of 54 patients (91%) had died. The median survival time was 15.7 months. Patients with the C allele variant at SNP rs12553173 (c.249T>C) had improved overall survival compared to those without (median survival: 27.3 vs. 13.6 months, p=0.0431). All other variants were not associated with overall survival. Likewise, high CAIX expression was associated with longer median survival (25.5 vs. 8.5 months, p<0.0001), as published previously [25, 31, 32]. We fit a multivariate Cox proportional hazards model to identify factors that were independently associated with overall survival. In this model, ECOG PS, T stage, CAIX expression and rs12553173 were identified as independent prognostic factors (Table 4).

Of the 54 patients, 43 (79%) received IL-2 based immunotherapy post nephrectomy. For the assessment of response, complete responses (CR) and partial responses (PR) were pooled into one group and compared to non-responders (stable disease, progressive disease). Four out of 7 (57%) patients with rs12553173 who had received IL-2 responded compared with 8 of 36 (22%) without rs12553173 (p=0.081). In contrast, rs2071676 (p=0.168), rs3829078 (p=0.123), rs1048638 (p=0.484) were all not associated with response to IL-2. In terms of CAIX protein expression, the response rate to IL-2 was 37% ($^{11}/_{30}$) in patients with high and 8% ($^{1}/_{13}$) in patients with low CAIX expression (p=0.070). All four CRs were observed in patients with high CAIX.

Discussion

We analyzed the CA9 gene coding sequence, CAIX protein expression and their association with survival and response to IL-2 in 54 Caucasian clear cell MRCC patients. We found 4 different SNPs in 2 of the 11 CA9 exons and the 3' UTR region, of which occurrence of rs12553173 (c.249T>C, exon 1) was associated with improved overall survival and retained as an independent prognostic factor in multivariate analysis. Furthermore, presence of the variant rs12553173 yielded a greater likelihood of response to IL-2 based immunotherapy. As described previously by us and others [25, 31, 32], high CAIX protein expression was associated with longer survival and a greater IL-2 response rate.

SNPs have been associated with survival in several cancer entities [1]-[17], but to date not in RCC. Furthermore, the current study is the first showing that a synonymous SNP is associated with survival in any type of cancer. As a synonymous CA9 SNP, rs12553173 does not alter the sequence of the CAIX protein. Until recently, synonymous SNPs were regarded as non-relevant, because it was thought that they are not able to affect expression and function of the related proteins. During the past years, however, several groups have pointed out that occurrence of synonymous SNPs do have an impact on the occurrence and course of diseases [10]. Kimchi-Sarfaty et al. [33] studied the synonymous SNP 1236C>T, the synonymous SNP 3435C>T and the non-synonymous 2677G>T SNP in the MDR1 gene, which plays a role in the development of resistance to chemotherapy. They found that the synonymous SNP 3435C>T is the key polymorphism of this haplotype, and that the non-synonymous SNP alone has no effect on the protein. A study of Laws et al. [34] showed that a synonymous SNP in the apoE gene carries a higher risk to develop Alzheimer. Capon et al. [35] found a synonymous SNP in the corneodesmosin gene, which may lead to psoriasis. The mechanisms how synonymous SNPs affect the protein are not completely understood. Current findings suggest that a synonymous SNP can change the amount, the structure and/or the function of a protein by three key mechanisms: 1) impacting mRNA structure and stability, 2) impacting kinetics of translation, and 3) alternating splicing [33]. Which mechanisms are responsible for improved survival of patients with rs12553173, remains elusive.

The CA9 gene encodes for the CAIX protein, which is widely regarded as one of the most significant molecular markers in MRCC [36]. Several studies have investigated the role of CAIX protein expression in MRCC and have consistently shown that high tumoral CAIX expression is associated with better prognosis and a greater likelihood of response to IL-2 based immunotherapy [37, 38]. This study represents yet another confirmation of the importance of CAIX protein in predicting survival and IL-2 response in MRCC. We further hypothesized that CA9 SNPs would be associated with CAIX protein expression. However, this association was not clearly observed. More importantly, both CA9 SNP rs12553173 and CAIX expression were complementary in predicting prognosis and both retained as independent prognostic factors of overall survival.

However, they did not correlate their findings with survival. The current study serves as another example that genetic (rs12553173) and protein information (CAIX expression) can predict prognosis of MRCC and should be integrated into future prognostic models and clinical care algorithms.

This study has several limitations. We investigated CA9 SNPs in tumor tissue and not in the blood, which was not possible because of the retrospective nature of this study. However, the SNPs that were detected are well described, and it is very unlikely that sequencing of CA9 in leukocytes would have yielded other results.

TABLE 1

Primers used in the study

| Exon(s) | Direction | Primer sequence | | SEQ ID NO: | Annealing Temperature (° C.) |
|---|---|---|---|---|---|
| 1 | Forward | 5'- -3' | gactttggctccatctctgc | 4 | 60 |
|   | Reverse | 5'- -3' | ctggaacctggatttggaga | 5 |   |
| 2-3 | Forward | 5'- -3' | cgtttgtgacatcgttttgg | 6 | 60 |
|   | Reverse | 5'- -3' | gccccatccccaagtctc | 7 |   |

TABLE 1-continued

Primers used in the study

| Exon(s) | Direction | Primer sequence | SEQ ID NO: | Annealing Temperature (° C.) |
|---|---|---|---|---|
| 4-5 | Forward | 5'- -3' ctcacttgcctctccctacg | 8 | 60 |
|  | Reverse | 5'- -3' atagagtccgggaggagcat | 9 |  |
| 6 | Forward | 5'- -3' agctgaggaatgggagaggt | 10 | 60 |
|  | Reverse | 5'- -3' cagacctgaagctccaaagg | 11 |  |
| 7 | Forward | 5'- -3' aagctttaaggggtgcaat | 12 | 60 |
|  | Reverse | 5'- -3' ccactgtgtccacacacacc | 13 |  |
| 8-9 | Forward | 5'- -3' cacccacactgtccactgac | 14 | 60 |
|  | Reverse | 5'- -3' aaaaggagagggagcagagg | 15 |  |
| 10-11 | Forward | 5'- -3' ggcaggtgttgaggaactct | 16 | 60 |
|  | Reverse | 5'- -3' ggggaacaaaggtgac-taaca | 17 |  |

TABLE 2

Patient and tumor characteristics, CAIX expression and CA9 gene status in 54 patients with metastatic clear cell RCC

| Gender, Age | ECOG PS | TNM stage, Fuhrman grade | No. of M1 sites | FU months, status | CAIX expression % | CA9 Exon 1 c.201G > A | CA9 Exon 1 c.249T > C | CA9 Exon 7 c.1081A > G | CA9 Exon 11 c.1584C > A |
|---|---|---|---|---|---|---|---|---|---|
| M, 69 | 2 | T3 N0 M1 G3 | 2 | 2, dead | 46.5 | Hetero |  |  | hetero |
| M, 51 | 1 | T3 N2 M1 G3 | 1 | 95.3, alive | 86.7 |  |  |  |  |
| F, 64 | 2 | T3 N0 M1 G2 | 3 | 19.9, dead | 70.0 |  |  |  |  |
| M, 71 | 1 | T3 N0 M1 G3 | 2 | 15.1, dead | 100.0 | Homo |  |  |  |
| M, 78 | 1 | T3 N0 M1 G2 | 2 | 27.3, dead | 100.0 | Hetero | hetero | hetero |  |
| M, 57 | 1 | T3 N0 M1 G2 | 2 | 35.5, alive | 100.0 |  | homo | hetero |  |
| M, 75 | 1 | T3 N0 M1 G2 | 1 | 10.7, dead | 100.0 |  |  |  |  |
| M, 69 | 1 | T2 N0 M1 G3 | 1 | 61.5, dead | 100.0 |  |  |  |  |
| F, 46 | 1 | T1 N0 M1 G2 | 2 | 23.3, dead | 80.0 | Homo |  |  | hetero |
| M, 65 | 1 | T1 N0 M1 G3 | 1 | 34.8, dead | 100.0 | Hetero |  |  |  |
| M, 55 | 0 | T3 N0 M1 G2 | 3 | 75.5, alive | 100.0 |  |  |  |  |
| M, 68 | 1 | T1 N0 M1 G2 | 1 | 122.9, dead | 100.0 |  | hetero |  |  |
| M, 67 | 2 | T4 N2 M1 G3 | 2 | 1.8, dead | 90.0 | Homo |  |  | hetero |
| F, 67 | 1 | T1 N0 M1 G2 | 1 | 20.8, dead | 0.0 | Homo |  |  |  |
| M, 58 | 1 | T3 N0 M1 G3 | 2 | 10.4, dead | 100.0 |  |  |  |  |
| M, 65 | 1 | T3 N0 M1 G2 | 1 | 8, dead | 100.0 |  |  |  |  |
| F, 52 | 0 | T3 N0 M1 G2 | 1 | 15.8, dead | 100.0 | Homo |  |  |  |
| M, 71 | 1 | T4 N1 M1 G4 | 3 | 10.2, dead | 85.0 | Hetero |  |  | hetero |
| M, 66 | 0 | T4 N0 M1 G3 | 2 | 62.3, dead | 100.0 | Hetero |  |  | hetero |
| M, 52 | 1 | T3 N0 M1 G2 | 2 | 21.8, dead | 100.0 | Hetero |  |  | hetero |
| M, 57 | 0 | T3 N0 M1 G2 | 2 | 39.7, dead | 26.7 | Hetero |  |  | hetero |
| M, 63 | 0 | T3 N0 M1 G2 | 2 | 81.6, alive | 100.0 | Homo |  |  | hetero |
| M, 65 | 0 | T3 N0 M1 G2 | 1 | 114.1, dead | 100.0 | Hetero | hetero | hetero |  |
| M, 66 | 1 | T3 N0 M1 G3 | 1 | 75.5, dead | 100.0 |  | hetero | hetero |  |
| F, 68 | 1 | T3 N2 M1 G2 | 1 | 2.9, dead | 70.0 | Hetero |  |  | hetero |
| M, 70 | 1 | T1 N0 M1 G3 | 2 | 108.1, dead | 98.0 |  |  |  |  |
| F, 74 | 1 | T3 N0 M1 G3 | 1 | 24.4, dead | 100.0 | Hetero | hetero | hetero |  |
| M, 66 | 1 | T3 N2 M1 G3 | 2 | 4.3, dead | 100.0 |  | hetero |  |  |
| M, 48 | 1 | T3 N0 N1 G3 | 2 | 2.3, dead | 1.7 | Homo |  |  | hetero |
| M, 68 | 0 | T3 N0 M1 G3 | 1 | 40.6, dead | 100.0 | Homo |  |  |  |
| M, 59 | 1 | T4 N0 M1 G2 | 1 | 1.4, dead | 100.0 |  |  |  |  |
| F, 66 | 1 | T3 N0 M1 G2 | 4 | 5.8, dead | 96.7 | Hetero |  |  | hetero |
| M, 48 | 1 | T4 N0 M1 G3 | 2 | 2.8, dead | 83.3 |  |  |  |  |
| M, 58 | 1 | T3 N0 M1 G3 | 2 | 8.5, dead | 41.3 | Hetero |  |  | hetero |
| M, 40 | 1 | T2 N0 M1 G2 | 1 | 12.2, dead | 70.0 | Homo |  |  |  |
| M, 34 | 1 | T3 N2 M1 G3 | 2 | 13.2, dead | 6.1 | Hetero | hetero | homo |  |
| F, 53 | 1 | T1 N1 M1 G4 | 3 | 10.8, dead | 0.0 | Hetero |  |  | hetero |
| M, 74 | 0 | T3 N0 M1 G2 | 2 | 24.9, dead | 92.5 | Hetero |  |  | hetero |
| M, 71 | 0 | T3 N0 M1 G2 | 1 | 31.6, dead | 100.0 | Homo |  |  | homo |
| M, 74 | 2 | T1 N0 M1 G2 | 1 | 13.6, dead | 11.0 |  |  |  | homo |
| F, 69 | 1 | T2 N0 M1 G1 | 1 | 23.6, dead | 100.0 |  |  |  |  |
| M, 50 | 1 | T4 N1 M1 G2 | 2 | 2.7, dead | 0.8 |  |  |  |  |
| F, 48 | 1 | T2 N2 M1 G3 | 1 | 85.6, dead | 100.0 |  |  |  |  |
| F, 64 | 1 | T3 N2 M1 G3 | 2 | 2, dead | 100.0 | Hetero |  |  |  |
| M, 68 | 1 | T3 N1 M1 G3 | 2 | 0.9, dead | 77.6 | Hetero |  |  |  |
| M, 62 | 0 | T3 N0 M1 G3 | 2 | 10.9, dead | 100.0 | Hetero |  |  |  |
| M, 54 | 1 | T3 N0 M1 G2 | 2 | 25.5, dead | 100.0 |  |  |  |  |
| M, 47 | 1 | T3 N0 M1 G4 | 1 | 12, dead | 100.0 | Hetero |  |  |  |

TABLE 2-continued

Patient and tumor characteristics, CAIX expression and CA9 gene status in 54 patients with metastatic clear cell RCC

| Gender, Age | ECOG PS | TNM stage, Fuhrman grade | No. of M1 sites | FU months, status | CAIX expression % | CA9 Exon 1 c.201G > A | CA9 Exon 1 c.249T > C | CA9 Exon 7 c.1081A > G | CA9 Exon 11 c.1584C > A |
|---|---|---|---|---|---|---|---|---|---|
| F, 63 | 1 | T3 N0 M1 G2 | 1 | 4.7, dead | 65.0 | | | | |
| M, 68 | 0 | T2 N0 M1 G3 | 2 | 5.6, dead | 79.0 | | | | |
| M, 51 | 0 | T3 N2 M1 G3 | 2 | 90.8, alive | 100.0 | Homo | | | hetero |
| M, 59 | 1 | T3 N1 M1 G3 | 2 | 26.9, dead | 100.0 | Hetero | | | |
| M, 51 | 1 | T3 N2 M1 G2 | 3 | 2.4, dead | 25.0 | | | | |
| M, 54 | 0 | T3 N0 M1 G2 | 1 | 23.1, dead | 100.0 | Hetero | | | hetero |

TABLE 3

Multivariate Cox proportional hazards model. ECOG PS, T stage, CAIX expression and CA9 SNP c.249T > C were all retained as independent prognostic factors of overall survival.

| | Categories | HR | 95.0% CI | | p-value |
|---|---|---|---|---|---|
| ECOG PS | ≥1 vs. 0 | 4.982 | 2.136 | 11.620 | 0.0002 |
| T stage | T¾ vs. T½ | 4.338 | 1.849 | 10.177 | 0.0007 |
| N stage | N+ vs. N0 | 0.615 | 0.275 | 1.378 | 0.2378 |
| Fuhrman grade | G¾ vs. G½ | 1.153 | 0.583 | 2.280 | 0.6820 |
| Metastatic sites | ≥2 vs. 1 | 1.040 | 0.548 | 1.974 | 0.9036 |
| CAIX expression | Continuous | 0.983 | 0.973 | 0.993 | 0.0005 |
| CA9 SNP rs12553173 | Yes vs. No | 0.234 | 0.087 | 0.628 | 0.0039 |

In an independent group of additional ~20 patients, preliminary studies continue to find that in patients with metastatic clear cell tumors, SNP1 is a significant predictor of survival in a multivariate model that includes the CAIX status and whether or not the patients received cytokine immunotherapy:

| | CC, M1 (n = 24) | | | |
|---|---|---|---|---|
| Variable | HR | HR low | HR high | p |
| SNP1 | 0.163 | 0.035 | 0.753 | 0.0201 |
| IMMUNO | 0.033 | 0.005 | 0.220 | 0.0004 |
| CAIX | 0.984 | 0.971 | 0.997 | 0.0135 |

TABLE 4

Variants, position, function, amino acid changes, and frequency of the observed CA9 sequence variations. Data according to NCBI database (http://www.ncbi.nlm.nih.gov/projects/SNP/).

| Exon | Contig position | cDNA position and nucleotide change | mRNA position | dbSNP rs# cluster id | Function | dbSNP allele | Protein residue | Codon position | Current study, Frequency Hetero | Homo | Total |
|---|---|---|---|---|---|---|---|---|---|---|---|
| 1 | 35664053 | c.201G > A | 139 | rs2071676 | Non-synonymous | GTG > ATG | Val[V] > Met[M] | 1 | 0.39 | 0.20 | 0.59 |
| 1 | 35664101 | c.249T > C | 187 | rs12553173 | Synonymous | TTG > CTG | Leu[L] > Leu[L] | 1 | 0.13 | 0.02 | 0.15 |
| 7 | 35669251 | c.1081A > G | 1019 | rs3829078 | Non-synonymous | CAA > CGA | Gln[Q] > Arg[R] | 2 | 0.09 | 0.02 | 0.11 |
| 11 | 35671122 | C.1584C > A | 1522 | rs1048638 | 3'UTR | A/C | — | — | 0.30 | 0.04 | 0.33 |

REFERENCES

[1] Jemal A, Siegel R, Ward E, Murray T, Xu J, Thun M J. Cancer statistics, 2007. CA Cancer J Clin 2007 January; 57(1):43-66.

[2] Figlin R A. Renal cell carcinoma: management of advanced disease. J Urol 1999 February; 161(2):381-6.

[3] Amato R J. Chemotherapy for renal cell carcinoma. Semin Oncol 2000 April; 27(2):177-86.

[4] Nanus D M, Garino A, Milowsky M I, Larkin M, Dutcher J P. Active chemotherapy for sarcomatoid and rapidly progressing renal cell carcinoma. Cancer 2004 Oct. 1; 101(7):1545-51.

[5] Motzer R J, Bacik J, Murphy B A, Russo P, Mazumdar M. Interferon-alfa as a comparative treatment for clinical trials of new therapies against advanced renal cell carcinoma. J Clin Oncol 2002 Jan. 1; 20(1):289-96.

[6] Kim H L, Seligson D, Liu X, et al. Using tumor markers to predict the survival of patients with metastatic renal cell carcinoma. J Urol 2005 May; 173(5):1496-501.

[7] Jones J, Otu H H, Grall F, et al. Proteomic identification of interleukin-2 therapy response in metastatic renal cell cancer. J Urol 2008 February; 179(2):730-6.

[8] Ito N, Eto M, Nakamura E, et al. STAT3 polymorphism predicts interferon-alfa response in patients with metastatic renal cell carcinoma. J Clin Oncol 2007 Jul. 1; 25(19):2785-91.

[9] Jones J, Otu H, Spentzos D, et al. Gene signatures of progression and metastasis in renal cell cancer. Clin Cancer Res 2005 Aug. 15; 11(16):5730-9.

[10] Sauna Z E, Kimchi-Sarfaty C, Ambudkar S V, Gottesman M M. Silent polymorphisms speak: how they affect pharmacogenomics and the treatment of cancer. Cancer Res 2007 Oct. 15; 67(20):9609-12.

[11] Papadopoulou E, Tripsianis G, Anagnostopoulos K, et al. The influence of serum HER-2 levels and HER-2 codon 655 polymorphism on breast cancer outcome. Neoplasma 2008; 55(2):113-21.

[12] Hughes S, Agbaje O, Bowen R L, et al. Matrix metalloproteinase single-nucleotide polymorphisms and haplotypes predict breast cancer progression. Clin Cancer Res 2007 Nov. 15; 13(22 Pt 1):6673-80.

[13] Domingo-Domenech E, Benavente Y, Gonzalez-Barca E, et al. Impact of interleukin-10 polymorphisms (−1082 and −3575) on the survival of patients with lymphoid neoplasms. Haematologica 2007 November; 92(11):1475-81.

[14] Tse K P, Tsang N M, Chen K D, et al. MCP-1 Promoter Polymorphism at 2518 is associated with metastasis of nasopharyngeal carcinoma after treatment. Clin Cancer Res 2007 Nov. 1; 13(21):6320-6.

[15] Decock J, Long J R, Laxton R C, et al. Association of matrix metalloproteinase-8 gene variation with breast cancer prognosis. Cancer Res 2007 Nov. 1; 67(21):10214-21.

[16] Chen Y C, Kraft P, Bretsky P, et al. Sequence variants of estrogen receptor beta and risk of prostate cancer in the National Cancer Institute Breast and Prostate Cancer Cohort Consortium. Cancer Epidemiol Biomarkers Prey 2007 October; 16(10): 1973-81.

[17] Bachmann H S, Otterbach F, Callies R, et al. The AA genotype of the regulatory BCL2 promoter polymorphism (938C>A) is associated with a favorable outcome in lymph node negative invasive breast cancer patients. Clin Cancer Res 2007 Oct. 1; 13(19):5790-7.

[18] Moch H, Presti J C, Jr., Sauter G, et al. Genetic aberrations detected by comparative genomic hybridization are associated with clinical outcome in renal cell carcinoma. Cancer Res 1996 Jan. 1; 56(1):27-30.

[19] Brunelli M, Eccher A, Gobbo S, et al. Loss of chromosome 9p is an independent prognostic factor in patients with clear cell renal cell carcinoma. Mod Pathol 2007 Sep. 28.

[20] Schraml P, Struckmann K, Bednar R, et al. CDKNA2A mutation analysis, protein expression, and deletion mapping of chromosome 9p in conventional clear-cell renal carcinomas: evidence for a second tumor suppressor gene proximal to CDKN2A. Am J Pathol 2001 February; 158(2):593-601.

[21] Ivanov S, Liao S Y, Ivanova A, et al. Expression of hypoxia-inducible cell-surface transmembrane carbonic anhydrases in human cancer. Am J Pathol 2001 March; 158(3):905-19.

[22] Atkins M, Regan M, McDermott D, et al. Carbonic anhydrase IX expression predicts outcome of interleukin 2 therapy for renal cancer. Clin Cancer Res 2005 May 15; 11(10):3714-21.

[23] Bui M H, Seligson D, Han K R, et al. Carbonic anhydrase IX is an independent predictor of survival in advanced renal clear cell carcinoma: implications for prognosis and therapy. Clin Cancer Res 2003 February; 9(2):802-11.

[24] Tripathi R T, Heilbrun L K, Jain V, Vaishampayan U N. Racial disparity in outcomes of a clinical trial population with metastatic renal cell carcinoma. Urology 2006 August; 68(2):296-301.

[25] Bui M H, Seligson D, Han K R, et al. Carbonic anhydrase IX is an independent predictor of survival in advanced renal clear cell carcinoma: implications for prognosis and therapy. Clin Cancer Res 2003 February; 9(2):802-11.

[26] Pantuck A J, Zeng G, Belldegrun A S, Figlin R A. Pathobiology, prognosis, and targeted therapy for renal cell carcinoma: exploiting the hypoxia-induced pathway. Clin Cancer Res 2003 Oct. 15; 9(13):4641-52.

[27] Oken M M, Creech R H, Tormey D C, et al. Toxicity and response criteria of the Eastern Cooperative Oncology Group. Am J Clin Oncol 1982 December; 5(6):649-55.

[28] Sobin L H, Wittekind C. Kidney. In: UICC International Union Against Cancer, editor. TNM classification of malignant tumors. 6 edn. Ed Willey-Liss.; 2003. p. 193-5.

[29] Fuhrman S A, Lasky L C, Limas C. Prognostic significance of morphologic parameters in renal cell carcinoma. Am J Surg Pathol 1982 October; 6(7):655-63.

[30] Kononen J, Bubendorf L, Kallioniemi A, et al. Tissue microarrays for high-throughput molecular profiling of tumor specimens. Nat Med 1998 July; 4(7):844-7.

[31] Atkins M, Regan M, McDermott D, et al. Carbonic anhydrase IX expression predicts outcome of interleukin 2 therapy for renal cancer. Clin Cancer Res 2005 May 15; 11(10):3714-21.

[32] Sandlund J, Oosterwijk E, Grankvist K, Oosterwijk-Wakka J, Ljungberg B, Rasmuson T. Prognostic impact of carbonic anhydrase IX expression in human renal cell carcinoma. BJU Int 2007 September; 100(3):556-60.

[33] Kimchi-Sarfaty C, Oh J M, Kim I W, et al. A "silent" polymorphism in the MDR1 gene changes substrate specificity. Science 2007 Jan. 26; 315(5811):525-8.

[34] Laws S M, Hone E, Gandy S, Martins R N. Expanding the association between the APOE gene and the risk of Alzheimer's disease: possible roles for APOE promoter polymorphisms and alterations in APOE transcription. J Neurochem 2003 March; 84(6):1215-36.

[35] Capon F, Allen M H, Ameen M, et al. A synonymous SNP of the corneodesmosin gene leads to increased mRNA stability and demonstrates association with psoriasis across diverse ethnic groups. Hum Mol Genet. 2004 Oct. 15; 13(20):2361-8.

[36] Leppert J T, Lam J S, Pantuck A J, Figlin R A, Belldegrun A S. Carbonic anhydrase IX and the future of molecular markers in renal cell carcinoma. BJU Int 2005 August; 96(3):281-5.

[37] Atkins M, Regan M, McDermott D, et al. Carbonic anhydrase IX expression predicts outcome of interleukin 2 therapy for renal cancer. Clin Cancer Res 2005 May 15; 11(10):3714-21.

[38] Bui M H, Seligson D, Han K R, et al. Carbonic anhydrase IX is an independent predictor of survival in advanced renal clear cell carcinoma: implications for prognosis and therapy. Clin Cancer Res 2003 February; 9(2):802-11.

[39] Motzer R J, Hutson T E, Tomczak P, et al. Sunitinib versus interferon alfa in metastatic renal-cell carcinoma. N Engl J Med 2007 Jan. 11; 356(2):115-24.

[40] Escudier B, Eisen T, Stadler W M, et al. Sorafenib in advanced clear-cell renal-cell carcinoma. N Engl J Med 2007 Jan. 11; 356(2):125-34.

[41] Hudes G, Carducci M, Tomczak P, et al. Temsirolimus, interferon alfa, or both for advanced renal-cell carcinoma. N Engl J Med 2007 May 31; 356(22):2271-81.

[42] Zisman A, Pantuck A J, Wieder J, et al. Risk group assessment and clinical outcome algorithm to predict the natural history of patients with surgically resected renal cell carcinoma. J Clin Oncol 2002 Dec. 1; 20(23):4559-66.

What is claimed is:

1. A method of treating a human patient having metastatic renal cell carcinoma (MRCC), said method comprising:
   (a) obtaining a biological sample containing Carbonic Anhydrase 9 (CA9) nucleic acid from the patient;
   (b) analyzing the biological sample to determine whether the CA9 nucleic acid has a C allele at polymorphic site rs12553173, thereby determining whether the patient has a C allele at polymorphic site rs12553173;
   (c) determining that the patient has an increased likelihood of responding to an IL-2 immunotherapy when the patient has a C allele at polymorphic site rs12553173; and
   (d) administering the IL-2 immunotherapy to the patient having the C allele at polymorphic site rs12553173, thereby treating the patient.

2. The method of claim 1, wherein the MRCC is metastatic clear cell renal cell carcinoma.

3. The method of claim 1, wherein the nucleic acid is cDNA or RNA.

4. The method of claim 1, wherein the nucleic acid is genomic DNA.

5. The method of claim 1, wherein the biological sample is from a tumor.

6. The method of claim 1, wherein the biological sample is from a renal tumor or a metastatic lesion derived from a renal tumor.

7. The method of claim 1, wherein the analyzing step comprises amplifying the CA9 nucleic acid by polymerase chain reaction (PCR).

* * * * *

SEQUENCE LISTING

<160> NUMBER OF SEQ ID NOS: 17

<210> SEQ ID NO 1
<211> LENGTH: 459
<212> TYPE: PRT
<213> ORGANISM: Homo sapiens
<220> FEATURE:
<223> OTHER INFORMATION: human carbonic anhydrase 9 (CA9), carbonic anhydrase IX (CAIX), carbonic dehydratase, renal cell carcinoma (RCC)-associated protein G250, MN

<400> SEQUENCE: 1

```
Met Ala Pro Leu Cys Pro Ser Pro Trp Leu Pro Leu Leu Ile Pro Ala
 1               5                  10                  15

Pro Ala Pro Gly Leu Thr Val Gln Leu Leu Ser Leu Leu Leu Leu Leu
            20                  25                  30

Val Pro Val His Pro Gln Arg Leu Pro Arg Met Gln Glu Asp Ser Pro
        35                  40                  45

Leu Gly Gly Ser Ser Gly Glu Asp Asp Pro Leu Gly Glu Glu Asp
 50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350
```

```
Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455
```

<210> SEQ ID NO 2
<211> LENGTH: 1561
<212> TYPE: DNA
<213> ORGANISM: Homo sapiens
<220> FEATURE:
<223> OTHER INFORMATION: human carbonic anhydrase 9 (CA9), carbonic
      anhydrase IX (CAIX), carbonic dehydratase, renal cell carcinoma
      (RCC)-associated protein G250, MN cDNA
<220> FEATURE:
<221> NAME/KEY: CDS
<222> LOCATION: (43)...(1422)
<223> OTHER INFORMATION: CAIX

<400> SEQUENCE: 2

```
gcccgtacac accgtgtgct gggacacccc acagtcagcc gcatggctcc cctgtgcccc      60 agccctggc tccctctgtt gatcccggcc cctgctccag gcctcactgt gcaactgctg     120
ctgtcactgc tgcttctggt gcctgtccat ccccagaggt tgccccggat gcaggaggat     180
tccccctggg gaggaggctc ttctggggaa gatgacccac tgggcgagga ggatctgccc     240
agtgaagagg attcacccag agaggaggat ccacccggag aggaggatct acctggagag     300
gaggatctac ctggagagga ggatctacct gaagttaagc ctaaatcaga agaagagggc     360
tccctgaagt tagaggatct acctactgtt gaggctcctg agatcctcag aaccccag     420 aataatgccc acagggacaa agaagggat gaccagagtc attggcgcta tggaggcgac     480
ccgccctggc cccgggtgtc cccagcctgc gcgggccgct tccagtcccc ggtggatatc     540 cgccccagc tcgccgcctt ctgcccggcc ctgcgcccc tggaactcct gggcttccag     600
ctcccgccgc tcccagaact gcgcctgcgc aacaatggcc acagtgtgca actgaccctg     660
cctcctgggc tagagatggc tctgggtccc ggcggagt accgggctct gcagctgcat     720
ctgcactggg gggctgcagg tcgtccgggc tcggagcaca ctgtggaagg ccaccgtttc     780
cctgccgaga tccacgtggt tcacctcagc accgcctttg ccagagttga cgaggccttg     840
gggcgcccgg gaggcctggc cgtgttggcc gcctttctgg aggagggccc ggaagaaaac     900
agtgcctatg agcagttgct gtctcgcttg gaagaaatcg ctgaggaagg ctcagagact     960
caggtcccag actgacat atctgcactc ctgccctctg acttcagccg ctacttccaa     1020 tatgagggt ctctgactac accgccctgt gcccagggtg tcatctggac tgtgtttaac     1080
cagacagtga tgctgagtgc taagcagctc cacaccctct ctgacaccct gtggggacct     1140
ggtgactctc ggctacagct gaacttccga gcgacgcagc ctttgaatgg gcgagtgatt     1200
gaggcctcct tccctgctgg agtggacagc agtcctcggg ctgctgagcc agtccagctg     1260
```

```
aattcctgcc tggctgctgg tgacatccta gccctggttt ttggcctcct ttttgctgtc   1320
accagcgtcg cgttccttgt gcagatgaga aggcagcaca gaaggggaac caaaggggt   1380 gtgagctacc gcccagcaga ggtagccgag actggagcct agaggctgga tcttggagaa   1440
tgtgagaagc cagccagagg catctgaggg ggagccggta actgtcctgt cctgctcatt   1500
atgccacttc cttttaactg ccaagaaatt ttttaaaata aatatttata ataaaaaaaa   1560
a                                                                    1561
```

<210> SEQ ID NO 3
<211> LENGTH: 7242
<212> TYPE: DNA
<213> ORGANISM: Homo sapiens
<220> FEATURE:
<223> OTHER INFORMATION: human carbonic anhydrase 9 (CA9), carbonic
      anhydrase IX (CAIX), carbonic dehydratase, renal cell carcinoma
      (RCC)-associated protein G250, MN genomic sequence

<400> SEQUENCE: 3

```
gcccgtacac accgtgtgct gggacacccc acagtcagcc gcatggctcc cctgtgcccc   60 agccctggc tccctctgtt gatcccggcc cctgctccag gcctcactgt gcaactgctg   120
ctgtcactgc tgcttctggt gcctgtccat ccccagaggt tgccccggat gcaggaggat   180
tccccctggg gaggaggctc ttctggggaa gatgacccac tgggcgagga ggatctgccc   240
agtgaagagg attcacccag agaggaggat ccacccggag aggaggatct acctggagag   300
gaggatctac ctggagagga ggatctacct gaagttaagc ctaaatcaga agaagagggc   360
tccctgaagt tagaggatct acctactgtt gaggctcctg gagatcctca agaaccccag   420
aataatgccc acagggacaa agaagtaag tggtcatcaa tctccaaatc caggttccag   480
gaggttcatg actcccctcc catacccag cctaggctct gttcactcag ggaaggaggg   540
gagactgtac tccccacaga agcccttcca gaggtcccat accaatatcc ccatccccac   600
tctcggaggt agaaagggac agatgtggag agaaaataaa aagggtgcaa aaggagagag   660
gtgagctgga tgagatggga gagaaggggg aggctggaga agagaaaggg atgagaactg   720
cagatgagag aaaaaatgtg cagacagagg aaaaaaatag gtggagaagg agagtcagag   780
agtttgaggg gaaagaaaaa ggaaagcttg ggaggtgaag tgggtaccag agacaagcaa   840 gaaagagctgg tagaagtcat ctcatcttag gctacaatga ggaaattgag acctaggaag   900
aagggacaca gcaggtagag aaacgtggct tcttgactcc caagccagga atttggggaa   960
aggggttgga gaccatacaa ggcagaggga tgagtgggga gaagaaagaa gggagaaagg   1020
aaagatggtg tactcactca tttgggactc aggactgaag tgcccactca ctttttttt   1080 tttttttttt gagacaaact ttcacttttg ttgcccaggc tggagtgcaa tggcgcgatc   1140
tcggctcact gcaacctcca cctcccgggt tcaagtgatt ctcctgcctc agcctctagc   1200
caagtagctg cgattacagg catgcgccac cacgcccggc taattttgt attttttagta   1260 gagacggggt ttcgccatgt tggtcaggct ggtctcgaac tcctgatctc aggtgatcca   1320
accaccctgg cctcccaaag tgctgggatt ataggcgtga ccacagcgc ctggcctgaa   1380 gcagccactc acttttacag accctaagac aatgattgca agctggtagg attgctgttt   1440 ggcccacca gctgcggtgt tgagtttggg tgcggtctcc tgtgctttgc acctggcccg   1500
cttaaggcat ttgttacccg taatgctcct gtaaggcatc tgcgtttgtg acatcgtttt   1560
ggtcgccagg aagggattgg ggctctaagc ttgagcggtt catccttttc atttatacag   1620
```

-continued

```
gggatgacca gagtcattgg cgctatggag gtgagacacc cacccgctgc acagacccaa    1680
tctgggaacc cagctctgtg gatctcccct acagccgtcc ctgaacactg gtcccgggcg    1740
tcccacccgc cgcccaccgt cccacccct caccttttct acccgggttc cctaagttcc     1800
tgacctaggc gtcagacttc ctcactatac tctcccaccc caggcgaccc gccctggccc    1860
cgggtgtccc cagcctgcgc gggccgcttc cagtccccgg tggatatccg cccccagctc    1920
gccgccttct gccggccct cgcccccctg gaactcctgg gcttccagct cccgccgctc     1980
ccagaactgc gcctgcgcaa caatggccac agtggtgagg gggtctcccc gccgagactt    2040
ggggatgggg cggggcgcag ggaagggaac cgtcgcggca gtgcctgccc gggggttggg    2100
ctggccctac cgggcggggc cggctcactt gcctctccct acgcagtgca actgaccctg    2160
cctcctgggc tagagatggc tctgggtccc gggcggagt accgggctct gcagctgcat     2220
ctgcactggg gggctgcagg tcgtccgggc tcggagcaca ctgtggaagg ccaccgtttc    2280
cctgccgagg tgagcgcgga gctggccgag aaggggcaaa ggagcggggc ggagcggggc    2340
cagagacgtg gccctctcct accctcgtgt ccttttcaga tccacgtggt tcacctcagc    2400
accgcctttg ccagagttga cgaggccttg gggcgcccgg gaggcctggc cgtgttggcc    2460
gcctttctgg aggtaccaga tcctggacac cccctactcc ccgctttccc atcccatgct    2520
cctcccggac tctatcgtgg agccagagac cccatcccag caagctcact caggcccctg    2580
gctgacaaac tcattcacgc actgtttgtt catttaacac ccactgtgaa ccaggcacca    2640
gcccccaaca aggattctga agctgtaggt ccttgcctct aaggagccca gccagtgg     2700 gggaggctga catgacagac acataggaag gacatagtaa agatggtggt cacagaggag    2760
gtgacactta aagccttcac tggtagaaaa gaaaggagg tgttcattgc agaggaaaca     2820
gaatgtgcaa agactcagaa tatggcctat ttagggaatg gctacataca ccatgattag    2880
aggaggccag taagggaag ggatggtgag atgcctgcta ggttcactca ctcacttta      2940 tttatttatt tattttttg acagtctctc tgtcgcccag gctggagtgc agtggtgtga     3000
tcttgggtca ctgcaacttc cgcctcccgg gttcaaggga ttctcctgcc tcagcttcct    3060
gagtagctgg ggttacaggt gtgtgccacc atgcccagct aattttttt tgtattttta     3120 gtagacaggg tttcaccatg ttggtcaggc tggtctcaaa ctcctggcct caagtgatcc    3180
gcctgactca gcctaccaaa gtgctgatta caagtgtgag ccaccgtgcc cagccacact    3240
cactgattct ttaatgccag ccacacagca caaagttcag agaaatgcct ccatcatagc    3300
atgtcaatat gttcatactc ttaggttcat aatgttctta acattaggtt cataagcaaa    3360
ataagaaaaa agaataataa ataaaagaag tggcatgtca ggacctcacc tgaaaagcca    3420
aacacagaat catgaaggtg aatgcagagg tgacaccaac acaaaggtgt atatatggtt    3480
tcctgtgggg agtatgtacg gaggcagcag tgagtgagac tgcaaacgtc agaagggcac    3540
gggtcactga gagcctagta tcctaagtaa agtgggctct ctccctctct ctccagcttg    3600
tcattgaaaa ccagtccacc aagcttgttg gttcgcacag caagagtaca tagagtttga    3660
aataatacat aggattttaa gagggagaca ctgtctctaa aaaaaaaac aacagcaaca     3720 acaaaaagca acaaccatta caattttatg ttccctcagc attctcagag ctgaggaatg    3780
ggagaggtct atgggaaccc cccttcatgt tccggccttc agccatggcc ctggatacat    3840
gcactcatct gtcttacaat gtcatccccc aggagggccc ggaagaaaac agtgcctatg    3900
agcagttgct gtctcgcttg gaagaaatcg ctgaggaagg tcagtttgtt ggtctggcca    3960
ctaatctctg tggcctagtt cataaagaat caccctttgg agcttcaggt ctgaggctgg    4020
```

```
agatgggctc cctccagtgc aggagggatt gaagcatgag ccagcgctca tcttgataat    4080
aaccatgaag ctgacagaca cagttacccg caaacggctg cctacagatt gaaaaccaag    4140
caaaaaccgc cgggcacggt ggctcacgcc tgtaatccca gcactttggg aggccaaggc    4200
aggtggatca cgaggtcaag agatcaagac catcctggcc aacatggtga acccccatct    4260
ctactaaaaa tacgaaaaaa tagccaggcg tggtggcggg tgcctgtaat cccagctact    4320
cgggaggctg aggcaggaga atggcatgaa cccgggaggc agaagttgca gtgagccgag    4380
atcgtgccac tgcactccag cctgggcaac agagcgagac tcttgtctca aaaaaaaaa     4440
aaaaaagaa aaccaagcaa aaccaaaat gagacaaaaa aacaagacc aaaaaatggt       4500
gtttggaatt gtcaaggtca agtctggaga gctaaacttt ttctgagaac tgtttatctt   4560
taataagcat caaatatttt aactttgtaa atacttttgt tggaaatcgt tctcttctta   4620
gtcactcttg ggtcatttta aatctcactt actctactag acctttttagg tttctgctag  4680
actaggtaga actctgcctt tgcatttctt gtgtctgttt tgtatagtta tcaatattca   4740
tatttattta caagttattc agatcatttt ttcttttctt ttctttttttt ttttttttac  4800
atctttagta gagacagggt ttcaccatat tggccaggct gctctcaaac tcctgacctt   4860
gtgatccacc agcctcggcc tcccaaagtg ctgggattca ttttttcttt ttaatttgct   4920
ctgggcttaa acttgtggcc cagcactttta tgatggtaca cagagttaag agtgtagact  4980
cagacggtct tcttctttc cttctcttcc ttcctccctt ccctcccacc ttcccttctc    5040
tccttccttt ctttcttcct ctcttgcttc tcaggcctc ttccagttgc tccaaagccc    5100
tgtactttt tttgagttac gtcttatggg aagggcctgc acttagcgaa gaagtggtct   5160
cagagttgag ttaccttggc ttctgggagg tgaaactgta tccctatacc ctgaagcttt   5220
aaggggggtgc aatgtagatg agaccccaac atagatcctc ttcacaggct cagagactca  5280
ggtcccagga ctggacatat ctgcactcct gccctctgac ttcagccgct acttccaata   5340
tgaggggtct ctgactacac cgccctgtgc ccagggtgtc atctggactg tgtttaacca   5400
gacagtgatg ctgagtgcta agcaggtggg cctggggtgt gtgtggacac agtgggtgcg   5460
ggggaaagag gatgtaagat gagatgagaa acaggagaag aaagaaatca aggctgggct   5520
ctgtggctta cgcctataat cccaccacgt tgggaggctg aggtgggaga atggtttgag   5580
cccaggagtt caagacaagg cggggcaaca tagtgtgacc ccatctctac caaaaaaacc   5640
ccaacaaaac caaaaatagc cgggcatggt ggtatgcgcc tagtcccagc tactcaagga   5700
ggctgaggtg ggaagatcgc ttgattccag gagtttgaga ctgcagtgag ctatgatccc   5760
accactgcct accatcttta ggatacattt atttatttat aaaagaaatc aagaggctgg   5820
atggggaata caggagctgg agggtggagc cctgaggtgc tggttgtgag ctggcctggg   5880
acccttgttt cctgtcatgc catgaaccca cccacactgt ccactgacct ccctagctcc   5940
acaccctctc tgacaccctg tggggacctg gtgactctcg gctacagctg aacttccgag   6000
cgacgcagcc tttgaatggg cgagtgattg aggcctcctt ccctgctgga gtggacagca   6060
gtcctcgggc tgctgagcca ggtacagctt tgtctggttt cccccagcc agtagtccct    6120
tatcctccca tgtgtgtgcc agtgtctgtc attggtggtc acagcccgcc tctcacatct   6180
cctttttctc tccagtccag ctgaattcct gcctggctgc tggtgagtct gcccctcctc   6240
ttggtcctga tgccaggaga ctcctcagca ccattcagcc ccagggctgc tcaggaccgc   6300
ctctgctccc tctccttttc tgcagaacag accccaaccc caatattaga gaggcagatc   6360
```

```
atggtgggga ttcccccatt gtcccagag gctaattgat tagaatgaag cttgagaaat    6420
ctcccagcat ccctctcgca aaacaatccc ccccttttt ttaaagatag ggtctcactc    6480
tgttgcccag gctgggtgt tgtggcacga tcatagctca ctgcagcctc gaactcctag    6540
gctcaggcaa tccttttcacc ttagcttctc aaagcactgg gactgtaggc atgagccact    6600
gtgcctggcc ccaaacggcc cttttacttg gcttttagga agcaaaaacg gtgcttatct    6660
taccccttct cgtgtatcca ccctcatccc ttggctggcc tcttctggag actgaggcac    6720 tagggctgc ctgagaactc ggggcagggg tggtggagtg cactgaggca ggtgttgagg    6780
aactctgcag accctcttc cttcccaaag cagccctctc tgctctccat cgcaggtgac    6840
atcctagccc tggtttttgg cctcctttt gctgtcacca gcgtcgcgtt ccttgtgcag    6900
atgagaaggc agcacaggta ttacactgac ccttttcttca ggcacaagct ccccccaccc    6960
ttgtggagtc acttcatgca aagcgcatgc aaatgagctg ctcctgggcc agttttctga    7020
ttagcctttc ctgttgtgta cacacagaag gggaaccaaa gggggtgtga gctaccgccc    7080
agcagaggta gccgagactg gagcctagag gctggatctt ggagaatgtg agaagccagc    7140
cagaggcatc tgagggggag ccggtaactg tcctgtcctg ctcattatgc cacttccttt    7200
taactgccaa gaaatttttt aaaataaata tttataataa aa                      7242
```

<210> SEQ ID NO 4
<211> LENGTH: 20
<212> TYPE: DNA
<213> ORGANISM: Artificial Sequence
<220> FEATURE:
<223> OTHER INFORMATION: synthetic CAIX exon 1 PCR amplification forward
      primer

<400> SEQUENCE: 4
gactttggct ccatctctgc                                                20

<210> SEQ ID NO 5
<211> LENGTH: 20
<212> TYPE: DNA
<213> ORGANISM: Artificial Sequence
<220> FEATURE:
<223> OTHER INFORMATION: synthetic CAIX exon 1 PCR amplification reverse
      primer

<400> SEQUENCE: 5
ctggaacctg gatttggaga                                                20

<210> SEQ ID NO 6
<211> LENGTH: 20
<212> TYPE: DNA
<213> ORGANISM: Artificial Sequence
<220> FEATURE:
<223> OTHER INFORMATION: synthetic CAIX exon 2-3 PCR amplification
      forward primer

<400> SEQUENCE: 6
cgtttgtgac atcgttttgg                                                20

<210> SEQ ID NO 7
<211> LENGTH: 18
<212> TYPE: DNA
<213> ORGANISM: Artificial Sequence
<220> FEATURE:
<223> OTHER INFORMATION: synthetic CAIX exon 2-3 PCR amplification
      reverse primer

<400> SEQUENCE: 7
gccccatccc caagtctc                                                18

<210> SEQ ID NO 8
<211> LENGTH: 20
<212> TYPE: DNA
<213> ORGANISM: Artificial Sequence
<220> FEATURE:
<223> OTHER INFORMATION: synthetic CAIX exon 4-5 PCR amplification
      forward primer

<400> SEQUENCE: 8
ctcacttgcc tctccctacg                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic CAIX exon 4-5 PCR amplification
      reverse primer

<400> SEQUENCE: 9
atagagtccg ggaggagcat                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic CAIX exon 6 PCR amplification forward
      primer

<400> SEQUENCE: 10
agctgaggaa tgggagaggt                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic CAIX exon 6 PCR amplification reverse
      primer

<400> SEQUENCE: 11
cagacctgaa gctccaaagg                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic CAIX exon 7 PCR amplification forward
      primer

<400> SEQUENCE: 12
aagctttaag ggggtgcaat                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic CAIX exon 7 PCR amplification reverse
      primer

<400> SEQUENCE: 13

```
-continued ccactgtgtc cacacacacc                                            20

<210> SEQ ID NO 14
<211> LENGTH: 20
<212> TYPE: DNA
<213> ORGANISM: Artificial Sequence
<220> FEATURE:
<223> OTHER INFORMATION: synthetic CAIX exon 8-9 PCR amplification
      forward primer

<400> SEQUENCE: 14
cacccacact gtccactgac                                            20

<210> SEQ ID NO 15
<211> LENGTH: 20
<212> TYPE: DNA
<213> ORGANISM: Artificial Sequence
<220> FEATURE:
<223> OTHER INFORMATION: synthetic CAIX exon 8-9 PCR amplification
      reverse primer

<400> SEQUENCE: 15
aaaaggagag ggagcagagg                                            20

<210> SEQ ID NO 16
<211> LENGTH: 20
<212> TYPE: DNA
<213> ORGANISM: Artificial Sequence
<220> FEATURE:
<223> OTHER INFORMATION: synthetic CAIX exon 10-11 PCR amplification
      forward primer

<400> SEQUENCE: 16
ggcaggtgtt gaggaactct                                            20

<210> SEQ ID NO 17
<211> LENGTH: 21
<212> TYPE: DNA
<213> ORGANISM: Artificial Sequence
<220> FEATURE:
<223> OTHER INFORMATION: synthetic CAIX exon 10-11 PCR amplification
      reverse primer

<400> SEQUENCE: 17
ggggaacaaa ggtgactaac a                                          21
```